(12) United States Patent
Goldman

(10) Patent No.: US 6,844,149 B2
(45) Date of Patent: Jan. 18, 2005

(54) METHOD, SYSTEM, AND APPARATUS FOR MEASUREMENT AND RECORDING OF BLOOD CHEMISTRY AND OTHER PHYSIOLOGICAL MEASUREMENTS

(75) Inventor: Richard Mark Goldman, San Jose, CA (US)

(73) Assignee: International Business Machines Corporation, New York, NY (US)

( * ) Notice: Subject to any disclaimer, the term of this patent is extended or adjusted under 35 U.S.C. 154(b) by 0 days.

(21) Appl. No.: 09/895,588

(22) Filed: Jun. 29, 2001

(65) Prior Publication Data

US 2003/0003522 A1 Jan. 2, 2003

(51) Int. Cl.[7] .............................. C12Q 1/00; C12Q 1/54; G01N 15/00
(52) U.S. Cl. ........................ 435/4; 422/50; 422/68.1; 702/19; 435/14; 435/11; 435/18
(58) Field of Search .................. 435/4, 11, 14, 435/18; 422/50, 68.1; 702/19, 27; 703/11

(56) References Cited

U.S. PATENT DOCUMENTS

| | | | |
|---|---|---|---|
| 3,298,789 A | 1/1967 | Mast | 23/253 |
| 3,630,957 A | 12/1971 | Rey et al. | 252/408 |
| 4,017,261 A | 4/1977 | Svoboda et al. | 23/253 TP |
| 4,090,505 A * | 5/1978 | Mortara | 128/2.06 G |
| 4,200,435 A * | 4/1980 | Stroupe et al. | 23/230 B |
| 4,857,453 A | 8/1989 | Ullman et al. | 435/7 |
| 4,895,558 A * | 1/1990 | Cham | 604/4 |
| 4,935,346 A | 6/1990 | Phillips et al. | 435/14 |
| 4,947,858 A | 8/1990 | Smith | 128/696 |
| 5,059,394 A | 10/1991 | Phillips et al. | 422/68.1 |
| 5,059,525 A | 10/1991 | Bartl et al. | 435/13 |
| 5,135,716 A | 8/1992 | Thakore | 422/56 |
| 5,141,872 A | 8/1992 | Tamir | 436/71 |
| 5,179,005 A | 1/1993 | Phillips et al. | 435/14 |
| 5,185,247 A | 2/1993 | Ismail et al. | 435/14 |
| 5,215,886 A | 6/1993 | Patel et al. | 435/11 |
| 5,304,468 A | 4/1994 | Phillips et al. | 435/14 |
| 5,306,623 A | 4/1994 | Kiser et al. | 435/14 |
| 5,401,466 A | 3/1995 | Foltz et al. | 422/56 |
| 5,453,360 A | 9/1995 | Yu | 435/28 |
| 5,563,031 A | 10/1996 | Yu | 435/4 |
| 5,563,042 A | 10/1996 | Phillips et al. | 435/14 |
| 5,620,863 A | 4/1997 | Tomasco et al. | 435/14 |
| 5,695,949 A | 12/1997 | Galen et al. | 435/14 |
| 5,752,917 A | 5/1998 | Fuchs | 600/484 |
| 5,753,452 A | 5/1998 | Smith | 435/14 |
| 5,785,650 A | 7/1998 | Akasaka et al. | 600/300 |
| 5,911,687 A | 6/1999 | Sato et al. | 600/300 |
| 5,912,139 A | 6/1999 | Iwata et al. | 435/26 |
| 5,922,530 A | 7/1999 | Yu | 435/4 |
| 5,945,345 A * | 8/1999 | Blatt et al. | 436/518 |
| 5,974,124 A | 10/1999 | Schlueter, Jr. et al. | 379/106.02 |
| 5,974,262 A * | 10/1999 | Fuller et al. | 395/838 |
| 6,032,119 A * | 2/2000 | Brown et al. | 705/2 |
| 6,055,487 A * | 4/2000 | Margery et al. | 702/84 |
| 6,168,563 B1 * | 1/2001 | Brown | 600/301 |
| 6,403,384 B1 * | 6/2002 | Lea | 436/518 |

* cited by examiner

Primary Examiner—Ardin H. Marschel
(74) Attorney, Agent, or Firm—Romualdas Strimaitis; Richard Goldman

(57) ABSTRACT

A multi-component test strip for analyzing a plurality of blood components in a single blood sample. The test strip comprises a porous medium having a sample receiving region, and two or more sample analysis regions. The sample receiving region is fluidically in series with the two or more sample analysis regions, and the two or more sample analysis regions are fluidically in parallel with each other. The two or more sample analysis regions contain indicating reagents specific to two or more specific blood components. Also disclosed is a system using the test strip for blood characterization, and a method of blood characterization and analysis.

4 Claims, 9 Drawing Sheets

METHOD, SYSTEM, AND APPARATUS FOR MEASUREMENT AND RECORDING OF BLOOD CHEMISTRY AND OTHER PHYSIOLOGICAL MEASUREMENTS

FIELD OF THE INVENTION

The invention relates to methods, systems, and apparatus for in-vitro testing of blood specimens by means of visible light, in which the blood specimen is collected on a single, unitary, integral absorbent test strip, and analyzed blood components. The analysis is based on optical properties of blood components with indicators or series, sequences, or systems of indicators. A further aspect of the invention is storing blood component measurements, optionally with other biological, physiological, and medical data for analysis and transmission, for example, to a health care provider.

BACKGROUND

1. Background—medical. Diabetes and coronary artery disease are major killers, but ones that are capable of detection, monitoring, and management through blood chemistry.

a. Coronary Artery Disease. Far too many people still die, and die too young, from cardiovascular disease. The American Heart Association reports that cardiovascular disease still kills almost 1 million Americans each year. This is more than all cancer deaths combined.

Many of these deaths occur because of narrowed or blocked arteries (atherosclerosis). Cholesterol plays a significant role in this largely preventable condition. Atherosclerosis is a silent, painless process in which cholesterol-containing fatty deposits (plaques) accumulate on the walls of the arteries.

As plaques build up, the opening in the artery narrows. This reduces the flow of blood. If reduced flow occurs in the coronary (heart) arteries, it can lead to a type of chest pain called angina pectoris. As a plaque enlarges, the inner lining of the artery becomes roughened. A tear or rupture in the plaque may cause a blood clot to form. Such a clot can block the flow of blood or break free and plug an artery downstream. If the flow of blood to a part of the heart is stopped, a person will have a heart attack. If blood flow to a part of the brain stops, the person will have a stroke.

Many factors influence the clogging of arteries. Cholesterol is important in the process. Cholesterol is a waxy, fat-like substance (lipid). Although it's often discussed as if it were a poison, one can't live without it. Cholesterol is essential to the body's cell membranes, to the insulation of the nerves and to the production of certain hormones. It's used by the liver to make bile acids, which help digest the food. The confusion that clouds cholesterol is partly due to the way some people use the word. The term "cholesterol" is often a catchall term for both dietary cholesterol and the cholesterol in the blood.

Cholesterol exists in food as a dietary lipid. Cholesterol is present in animal products, such as meat and dairy foods. Cholesterol also exists in a different way as a natural component of the blood lipids. The cholesterol in the blood comes both from the liver and from dietary cholesterol. The liver makes about 80 percent of the blood cholesterol. Only about 20 percent comes from the diet. The amount of dietary fat and cholesterol may influence all levels of the blood lipids, including the blood cholesterol levels.

To be carried in the blood, the body coats cholesterol with proteins called apoproteins. Once coated, they form a package called lipoproteins. Lipoproteins carry both cholesterol and triglycerides (another blood lipid) in the blood. Some of the lipoproteins are called low-density lipoproteins (LDLs). They contain high levels of cholesterol. Others are called high-density lipoproteins (HDLs). They contain mostly protein. A third type of lipoprotein is called a very-low-density lipoprotein (VLDL). This type contains cholesterol, triglycerides and protein.

Cholesterol serves as a building material in cells throughout the body. LDL particles, which carry cholesterol, attach themselves to receptors on cell surfaces and are then received into the cells. If there are too many LDL particles in the blood, if the liver cells (LDL receptors) do not receive LDL particles normally, or, if there are too few LDL receptors in the liver, the body's cells become saturated with cholesterol from the LDL particles. Cholesterol is then deposited in the artery walls. At this point the high-density lipoproteins (HDLs) play their "good" role. They actually pick up cholesterol deposited in the artery walls and transport it to the liver for disposal. If too much cholesterol from LDL particles remains deposited in the artery walls, the arteries will develop plaques and begin to narrow. This is the atherosclerosis disease process. This is why a high HDL level relative the LDL level is good. It can help protect a person from developing atherosclerosis.

Many people have high cholesterol. High levels may result from genetic makeup, the existence of diabetes, or lifestyle choices, or all three.

The only way to find out if the blood lipids are in a desirable range is to have them tested. The test is done by taking a fasting blood sample, after the patient has fasted overnight. Health advocacy groups and respected medical centers recommend measuring the total cholesterol, HDL cholesterol and triglycerides. (Total cholesterol is made up of the LDL, HDL and other blood cholesterol particles.)

As people age, the level of LDL cholesterol usually increases. Researchers aren't sure why. The increase could be caused by aging or by an increase in the body fat. Additionally, until age 45, men generally have higher total cholesterol levels than women. Also, up to about this age, women tend to have higher HDL levels. However, after menopause, women's total cholesterol rises and the protective HDL drops unless they take hormone replacement therapy.

Hypercholesterol is a "family" disease and a disease of advancing age. If members of the family have undesirable lipid levels and cardiovascular problems, the risks for these problems are increased. Children in families in which adults have high cholesterol are more likely to have high cholesterol themselves. The early signs of atherosclerosis appear in childhood. It is important that children in "at risk" families have their glucose and cholesterol checked.

a. Diabetes. Like hypercholesterol, diabetes is a "family" disease and a disease of advancing age. Diabetes is a complex disease process involving either or both of (1) the insulin producing islets of Langerhans in the pancreas, and (2) the uptake of blood glucose by the cells.

Individuals suffering from diabetes have hyperglycemia, i.e., an abnormally high blood sugar level. Generally, in Type I diabetes ("insulin dependent" or "childhood onset" diabetes) the pancreas does not secrete sufficient amounts of insulin into the bloodstream to regulate carbohydrate metabolism. In Type II ("adult onset" or "non-insulin dependent" diabetes) the chemical activity of the insulin is insufficient to regulate carbohydrate utilization with either diabetic disease process. If an abnormally high blood sugar level is allowed to continue for prolonged periods, the individual will suffer from the chronic complications of diabetes, including retinopathy, nephropathy, neuropathy and cardiovascular disease.

Ninety percent of all diabetics are "Type II" diabetics. Associated with "adult onset" diabetes is a reduced chemical activity of the insulin produced by the pancreas, high cholesterol, a higher than normal LDL cholesterol fraction, a lower than normal HDL cholesterol fraction, elevated triglycerides, and inefficient glucose⇌glycogen formation. These are all constituents of the "plasma nutriment" or "energy storing" fraction of blood plasma. This set of conditions is associated with a single defective gene or set of genes, and appears to "run in families." When the clinician sees this set of symptoms, the goal is clear—bring down the glucose, the triglycerides, the cholesterol, and the LDL, and elevate the HDL. The clinician prescribes exercise, weight loss, dietary changes, glucose lowering drugs, cholesterol lowering drugs, and possibly hypertension drugs (since elevated blood pressure and coronary artery disease are also frequently present).

Diabetes can increase triglycerides and decrease HDL in many people. Diabetes accelerates the development of atherosclerosis, which, in turn, increases the risk for heart attack, stroke and reduced circulation to the feet. If a patient has diabetes, the total cholesterol, triglycerides and HDL must be tested frequently. This is a challenge for the patient and clinician because of changing health care practices, paradigms, and economics in the United States.

2. Background—Blood Chemistry. Blood circulates through the heart, arteries, veins, and capillaries, carrying nourishment, electrolytes, hormones, vitamins, antibodies, heat, and oxygen to body tissues, and taking away waste matter and carbon dioxide. Whole blood is composed of two fractions, cells and plasma.

The "cells" or "blood cell" fraction contains red blood cells (erythrocytes), white blood cells (leukocytes), and platelets. Red blood cells transport $O_2$ from the lungs to the cells and $CO_2$ from the cells to the lungs for exhalation. Each red blood cell contains four Fe atoms in a structure known as the hemoglobin molecule. Oxygen from the lungs combines with the hemoglobin molecule to form oxyhemoglobin for transport to the tissues, where it is given up to the tissues, and carbon dioxide taken up from the tissues. The carbon dioxide reacts with the hemoglobin to form carbaminohemoglobin. White blood cells carry antibodies to surround and destroy invading cells.

Whole blood also carries platelets. Platelets are the repair substance that initiates blood clotting and coagulation. Coagulation is a complex process in which thrombin, a protein, reacts on soluble fibrinogen to generate insoluble fibrin. Fibrin deposits as fine threads. The platelets cling to the fibrin threads.

The "cells" or blood cell fraction is about 45% by volume of the blood. The remaining 55% of the blood is a clear to straw colored liquid fraction called plasma. The plasma contains about 8 weight percent "solids." The plasma solids include plasma proteins (organic repair substances as albumins, fibrinogen, prothrombin, and globulin), nutriments (as glucose, triglycerides, cholesterol, other lipids, and amino acids), regulatory and protective substances (enzymes, hormones, and antibodies), electrolytes (potassium, sodium, and chloride), and metabolic waste (urea and uric acid).

3. Challenge—medical. The overarching medical challenge is to effectively control blood glucose, blood cholesterol, and lipoproteins. Studies indicate that diabetic patients who are able to maintain near normal glucose control greatly reduce the likelihood of such dire complications as retinopathy, nephropathy, neuropathy and cardiovascular disease. Other studies indicate that hypercholesteric patients who control their cholesterol and lipids, while raising their HDL cholesterol, can significantly reduce their risk of coronary disease.

Therefore, several tests have been developed to measure and control hyperglycemic and hypercholesteric conditions. These include (i) direct measurement of glucose (which has a half life on the order of hours), (ii) direct measurement of cholesterol and associated lipoproteins (which have a half life of 4–12 weeks), and (iii) measurement of glycosylated hemoglobin (which has a half life on the order of 4–12 weeks). For purposes of mathematical modeling, glycosylated hemoglobin may be considered as a form of a time integral of glucose. Additionally, there are clinical advantages to frequent measurement of lipids (cholesterol, HDL cholesterol, LDL cholesterol, and triglycerides) in diabetes management. This is because of the close association of other life threatening conditions and diabetic complications with abnormal values of each of these blood components.

The clinician bases her determination of the effectiveness of blood glucose and cholesterol control on, at most, a $75–$125 set of blood tests that, in today's age of HMO's and managed care, is done, at most, quarterly. However, glucose (a measure of insulin production and utilization) changes hour-by-hour, as do other plasma nutriments and insulin. Absent a pathology or other upset, lipids (cholesterol, LDL, HDL, triglycerides) change very slowly and have a half-life of weeks to months. But, diabetes is a "pathology" and prescribing medication is an "upset." And, there can be "trend lines", as from a change in diet ("bran muffins", psylium) or medication (statins), which can be important to the patient and the clinician. This is what the patient must be enabled and empowered to monitor, at home, with a user friendly system and method, and without invading veins or arteries.

Clearly, a need exists for a simple, easy to use, home blood nutriment quantitative analyzer, that can analyze for glucose, glycosylated hemoglobin, cholesterol (or cholesterol fractions), and triglycerides. The analyzer must be easy to use, inexpensive, reliable, accurate to within home health care diagnostic standards (but not necessarily to clinical or laboratory standards), rugged, and inexpensive, and require a "pin prick" or "pin stick" sample of capillary blood, without puncturing veins or arteries. This is to enable the sample to be drawn without the intervention of a trained technician in a hospital, doctor's office, or clinical setting. To the maximum extent possible, the system must be immune to improper usage ("user friendly" or "idiot proof").

4. Background—Blood Chemistry Testing. Of interest to the patient and clinician are the blood chemistry tests. The full range of blood chemistry tests available to the clinician determine and report pH, glucose, non-protein nitrogen, lipids, proteins, enzymes, and steroids. Of particular interest for home health monitoring—in the absence of specific pathologies or disease processes—are glucose, time-integrated glucose (glycosylated hemoglobin), and lipids (cholesterol including LDL and HDL, and triglycerides). Additionally, iron is frequently indicated for early detection of one or both of anemia and/or internal bleeding, and clotting factors, especially for patients on anti-coagulants (which are frequently prescribed for hypercholesteric patients who may also require coumadine as a prophylaxis).

Normally glucose and lipids are quantitatively determined by colorimeter/filter photometer, flame photometer, or spectrophotometer.

A colorimeter or filter photometer is an optical electronic device that measures the color, reflectivity, or light absorption properties of a solute (typically after reaction between the solute or solute-enzyme product and a dye or other reagent). The results are measured by a densitometer and displayed in terms of color transmittance or absorbance to indicate concentration of the component analyzed for.

A flame photometer is an optical instrument that measures the color intensity of a substance that has been aspirated into a flame.

A spectrophotometer is a sophisticated colorimeter that measures light absorption as a function of wavelength as a quantitative and qualitative test.

To be noted is that samples can be chromatographically separated and analyzed, even in a simple, porous, fibrous pad or strip, with results displayed as, for example, the intensities of colored bands or strips. Samples can also be analyzed in an autoanalyzer, which sequentially measures and displays blood chemistry analysis by sequentially passing the blood through the analyzer, and drawing off portions for analysis.

5. Background—Glucose Testing

The short half life of glucose, the even shorter half life of insulin, the inaccuracy of "sugar in the urine" and "ketones in the urine" tests, and the user unfriendliness of wet chemistry tests motivated the development of progressively more user friendly dry chemistry quantitative tests for blood glucose.

5. a. Background—Colorimetric Testing. The first home tests for glucose were colorimetric tests. These early tests, described in U.S. Pat. No. 3,298,789 to Mast et al. and U.S. Pat. No. 3,630,957 to Rey et al., utilized a timed exposure to an oxidase/peroxidase immobilized enzyme system and the color change visually determined. In the early colorimetric tests a sample of fresh, whole blood (typically 20–40 $\mu$l) was placed on an absorbent pad containing an immobilized enzyme system having glucose oxidase and peroxidase activity. The enzyme system reacted with the glucose in the blood sample and released hydrogen peroxide. The pad also contained an indicator which reacted with the hydrogen peroxide in the presence of peroxidase to give a color proportional in intensity to the sample's glucose level.

In these early tests the blood sample was allowed to remain in contact with the reagent pad for a specific time (typically one minute). Then, the blood sample was either washed off or wiped off the pad, and the color of the pad visually evaluated. The evaluation was made either by comparing color generated with a color chart or by placing the pad or film in a diffuse reflectance instrument to read a color intensity value.

These early tests were used in glucose monitoring for years, even though they had significant limitations. The sample size required was rather large for a finger stick test and was difficult to achieve for some people whose capillary blood does not express readily.

In addition, the result (glucose concentration) was based on an absolute color reading which is in turn related to the absolute extent of reaction between the sample and the test reagents. The fact that the sample had to be washed or wiped off the reagent pad after the timed reaction interval required that the user be ready at the end of the timed interval to promptly wipe or apply a wash stream at the required time. The fact that the reaction was stopped by removing the sample led to uncertainty in the result, especially in the hands of the home user. Overwashing gave low results and underwashing gave high results.

Another problem that often existed in simple end user colorimetric determinations is the necessity for initiating a separate timing sequence when blood is applied to a reagent pad. A user would typically have conducted a finger stick to obtain a blood sample and will then be required to simultaneously (1) apply the blood from the finger to a reagent pad while (2) initiating a timing circuit with his or her other hand, thereby requiring the use of both hands simultaneously. This is particularly difficult since it is often necessary to insure that the timing circuit is started only when blood is applied to the test strip. All of the prior art methods require additional manipulations or additional circuitry to achieve this result. Accordingly, simplification of this aspect of reflectance reading instruments is desirable.

The presence of red blood cells or other colored components often interfered with the measurements of these absolute color values, thereby calling for exclusion of red blood cells in the prior art methods as they were most widely practiced. This was typically accomplished by a size based separation (filtration) in or before the absorbent pad.

5. b. Background—Reflectance/Absorbance. The early home tests, described above, have been supplanted by reflectance/absorbance tests. These tests are described in, for example, U.S. Pat. No. 5,179,005 to Phillips et al., U.S. Pat. No. 4,935,346 to Phillips et al., U.S. Pat. No. 5,059,394 to Phillips et al., U.S. Pat. No. 5,304,468 to Phillips et al., and U.S. Pat. No. 5,563,042 to Phillips et al. In reflectance/absorbance testing the test strips have a hydrophilic porous matrix containing a "signal producing system" (colorimetric chemical reaction sequence beginning with an enzyme catalyzed reaction of glucose and ending with a chromophore) and used in conjunction with a reflectance measuring apparatus which is activated upon a change in reflectance of the hydrophilic porous matrix when blood penetrates the matrix. The method begins when a "pin prick" sample of whole blood is placed on an exposed surface of the hydrophilic matrix. The matrix performs a "rough cut" separation or fractionation or chromatographic separation of the blood, filtering out large particles, such as red blood cells. The "signal-producing system" produces a blood reaction product which further changes the reflectance of the matrix. This change can be related to the (quantitative) presence of a blood fraction in a sample.

5. c. Background—The Matrix—The hydrophilic matrix is central to dry chemistry glucose monitoring systems. The matrix is the internal element of the test strip. Bound to the matrix are one or more reagents of a "signal producing system". By a "signal producing system" is meant an enzyme and dye system that changes in some measurable optical property related to the glucose content of the blood. Specifically, the glucose reacts with an immobilized enzyme in the matrix. This results in the production of an enzyme reaction product (possibly after several reaction steps) provides a change in the amount of reflectance of the matrix. The matrix is typically present in a reflectance-measuring apparatus when blood is applied. The blood sample penetrates the matrix, resulting in an initial change in reflectance at the measurement surface. A reading is the taken one or more times after the initial change in reflectance. Further changes in reflectance at the measurement surface or in the matrix are the direct or indirect result of formation of the enzyme reaction product, and the correlation of the color change to the amount of glucose in the sample.

The porous matrix contains an immobilized oxidase enzyme system which produces hydrogen peroxide from the glucose. The matrix also contains a second immobilized enzyme, particularly a peroxidase, and a dye system which produces a light-absorbing product in conjunction with the peroxidase product. The light-absorbing enzyme reaction product changes the reflectance of the matrix system. Readings are taken at two different wavelengths, with the reading at one wavelength used to subtract any background interference caused by hematocrit, blood oxygenation, and other variables which may affect the result.

5. d. Background—The Chemical Reagents Any signal producing immobilized enzyme and dye system may be employed that is capable of reacting with the glucose in the sample to produce (either directly or indirectly) a compound that is reproducibly quantitatively absorptive at a wavelength other than a wavelength at which the assay medium substantially absorbs incident light. A substrate (glucose) reacts with an oxygen-utilizing oxidase enzyme so that an intermediate reaction product is produced. This intermediate reaction product further reacts with a dye intermediate to either directly or indirectly form a dye which absorbs in a predetermined wavelength range. For example, an oxidase enzyme can oxidize a glucose substrate and produce hydrogen peroxide as an intermediate reaction product. The hydrogen peroxide can then react with a dye intermediate or precursor, in a catalyzed or uncatalyzed reaction, to produce an oxidized form of the intermediate or precursor. This oxidized material may produce the colored product or react with a second precursor to form the final dye. This is shown in equations (1) and (2)

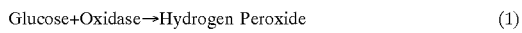

Glucose+Oxidase→Hydrogen Peroxide (1)

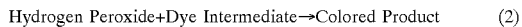

Hydrogen Peroxide+Dye Intermediate→Colored Product (2)

Typical immobilized enzymes include Glucose Oxidase, and Glucose Peroxidase for glucose.

5. e. The Glucose Analysis Method—The analysis method for glucose relies on a change in optical absorbance, as measured by diffuse reflectance. The diffuse reflectance is dependent upon the amount of glucose present in the sample being tested. The glucose concentration may be determined by measuring the change in the absorbance of the test sample between two or more points in time.

6. a. Background—The Meter The measurement instrument, as exemplified by glucose meters on the market, are diffuse reflectance spectrophotometers with appropriate software. A typical meter automatically reads reflectance at certain selected points in time, calculates the rate of reflectance change, and, using calibration factors, outputs the level of glucose in the blood. A blood glucose meter with a spectrophotometer has a structure for holding the matrix in proximity to a light source. The light source, which may be, for example, a high intensity light emitting diode (LED) or a laser, projects a beam of light onto the sample and enzyme product containing region of the porous matrix. A substantial portion (at least 25%, preferably at least 35%, and more preferably at least 50%, in the absence of reaction product) of this light is diffusely reflected from the porous matrix, and is detected by a light detector. The light detector can be, for example, a phototransistor that produces an output current proportional to the light it receives. In commercial systems, two wave lengths of light are used, 635 nm and 700 nm. This is because the chromophore produced by the glucose-enzyme reactions, and the subsequent reaction with the dye, has different optical characteristics at 635 nm and 700 nm.

6. b. Reflectance Switching The reflectance circuit itself can be used to initiate timing by measuring a drop in reflectance that occurs when the aqueous portion of the blood applied to the porous matrix, or reagent pad migrates through the matrix to the surface or zone at which reflectance is being measured. Typically, the measuring device is turned on in a "ready" mode in which reflectance readings are automatically made at closely spaced intervals (typically about 0.2 seconds) from the typically off-white, substantially dry, unreacted reagent strip. The initial measurement is typically made prior to penetration of the matrix by the blood being analyzed. The reflectance value is evaluated by the microprocessor, typically by storing successive values in memory and then comparing each value with the initial unreacted value. When the blood penetrates the reagent matrix pad the drop in reflectance signals the start of the measuring time interval. Drops in reflectance of 5–50% can be used to initiate timing, typically a drop of about 10% initiates timing. In this simple way there is exact synchronization of blood reaching the surface from which measurements are taken and initiation of the sequence of readings, with no requirement of activity by the user.

7. Background—glycosylated Hemoglobin Testing

The common, user friendly, home medical test to measure and control hyperglycemic conditions is the direct measurement of blood glucose levels by diabetics, as described above. Because blood glucose levels fluctuate significantly throughout a given day, being influenced by diet, activity, and treatment, depending on the nature and severity of the individual case, some patients measure their blood glucose levels many times a day. Based on the observed pattern in the measured glucose levels, the patient and physician together make adjustments in diet, exercise and insulin intake to better manage the disease. Clearly, this information should be available to the patient immediately.

Note that both insulin and glucose have very short residence times in the human body. For this reason, glucose measurements alone do not give an accurate picture of the patient's blood chemistry. The "instantaneous" glucose content is a function of time of day, meals, exercise, etc. For this reason, tests which are independent of a patient's diet, activity, and/or treatment and which provide longer term indications of blood glucose levels have also been developed. These tests measure the concentration of glycosylated proteins or "protein-bound glucose" (PBG). Proteins, such as those present in whole blood, serum and other biological fluids react with glucose, under non-enzymatic conditions, to produce glycosylated proteins. The extent of the reaction is directly dependent upon a "time integral" over days to months of the glucose concentration of the blood.

One of the first glycosylated protein tests developed measures glycosylated hemoglobin, namely Hemoglobin $A_{1c}$ (Hb$A_{1c}$). Hemoglobin $A_{1c}$ has a residence time in the human body on the order of weeks to months. The measurement of Hemoglobin $A_{1c}$ reflects glycemic control over approximately a 2 to 3 month period.

One way to indirectly assess blood sugar concentration through Hemoglobin $A_{1c}$ is to analyze fructosamine concentration. One dry fructosamine dry test system has been described in U.S. Pat. No. 5,695,949 to Galen et al. glycosylated proteins are also known as fructosamines or ketoamines. The blood proteins are glycosylated in vivo by a non-enzymatic reaction between glucose and available amino groups of blood proteins, principally the ε-amino groups of lysine residues and the α-amino groups of the protein's terminal amino acid. The glucose binds to an amino group of the protein to form a Schiff base, i.e., a glucosylamine or aldimine, that undergoes molecular rearrangement to form a stable ketoamine. Such ketoamines are generically known as "fructosamines." The degree of protein glycosolation and fructosamine formation is directly proportional to a "time integral" of the blood glucose concentration over time (e.g., about 2 to 3 months). Measurement of serum or plasma fructosamine levels is useful for monitoring diabetic control because fructosamine concentrations in serum or plasma reflect an average of blood glucose level over a period on the order of months.

While user friendly, home individual tests to directly and indirectly measure glucose have been developed, as described above, there has been no convenient, user-friendly, home test system available which allows a diabetic patient or a physician to assess both the immediate glucose level as well as an intermediate or long-term glycemic condition. Currently, while the glucose test is routinely run by the doctor or the patient, however, the glycosylated protein testing is typically performed in a clinical lab setting using complicated techniques and expensive instrumentation. Results from these clinical lab tests are usually not available to the doctor and patient for several days. This delay in information transfer decreases the value of the test result. The physician can even neglect to relay the test result to the patient until the next visit, which could be several months. It has been reported that doctors and patients who were made aware of their glycosylated protein test results had better glycemic control than those who were unaware of such results.

It is also now believed that glycosylated proteins, as well as hyperglycemia, can be the causative agents in disease complications. This is clinically significant and vital in detecting hyperglycemic problems before vision, cardiac, kidney, or circulatory problems arise. Thus, a need exists for conveniently and quickly measuring glycosylated protein alone, or in combination with glucose for determining the integrated glycemic condition of a subject.

Currently, no user-friendly test system exists which determines the integrated glycemic condition of a subject, providing the subject with a complete picture of his or her glycemic status, thus allowing for the best possible monitoring and treatment. Particularly useful would be a single instrument for determining a patient's integrated glycemic condition which could be used at the doctor's office, and at home by the diabetic patient.

Fructosamines are formed in vivo by glycosylated proteins. Under alkaline conditions, the fructosamines that form in the blood are converted in vitro to eneaminols. The eneaminol form of fructosamine is a chemically active reducing substance that reacts with a suitable indicator capable of being reduced by fructosamine. For example, the color transition of a chromogenic dye or the fluorescence of a fluorescent reagent resulting from this reaction can be measured and compared with a standard to give an indication of the average glucose concentration in blood samples over the prior half month period. In general, the fructosamine concentration in a blood, such as blood serum, reflects an average glucose concentration over a period of approximately a half month.

Clearly, a need exists to provide for glycosylated hemoglobin testing in combination with other blood fractions in a user-friendly test device.

8. Background—Lipid Testing (Including Cholesterol, Triglycerides, Low Density Lipoprotein (LDL) and High Density Lipoprotein)

8. a. Cholesterol Testing. U.S. Pat. No. 5,912,139 to Iwata describes a dry test for cholesterol. According to Iwata, an insert for dry test strip detection and measurement of cholesterol has been achieved by providing a test strip which comprises a carrier, a dehydrogenase (cholesterol dehydrogenase), diaphorase, a fluorescent chromogen and nicotinamide adenine dinucleotide (NAD) or nicotinamide adenine dinucleotide phosphate (NADP).

8. b. Triglyceride Testing—U.S. Pat. No. 5,912,139 to Iwata also describes a similar dry test for cholesterol. According to Iwata, an insert for dry test strip detection and measurement of triglycerides where the triglycerides are broken down to glycerols.

8. c. Lipoproteins

Lipoproteins are complex particles comprising proteins and lipids which are found in the circulatory system. One of their functions is to carry water insoluble substances, such as cholesterol and cholesterol esters, for eventual cellular utilization. While all cells require cholesterol for growth, the excess accumulation of cholesterol by cells can lead to certain diseases including arteriorsclerosis.

There are a variety of classes of lipoproteins in serum which can be classified by their density. These classes include very low density lipoproteins (VLDL), low density lipoproteins (LDL) and high density lipoproteins (HDL). All of these lipoproteins contain varying amounts of cholesterol. A total serum cholesterol determination is a complex sum of the amount that each lipoprotein contributes to the total lipoprotein population of the serum.

While it is known that the amount of total serum cholesterol can be correlated with the incidence of arteriorsclerosis, evidence from studies of recent years has shown that specific lipoprotein types are more closely associated with the progression of heart disease, including arteriorsclerosis, than other lipoprotein types. More recent studies have implicated LDL as the class of lipoproteins responsible for the accumulation of cholesterol in the cells while HDL has been shown to be active in the removal of excess cholesterol from cells. Moreover, other studies show a high correlation between Type II (adult onset) diabetes, hyperglycemia, elevated LDL, low HDL, and hypertension with arteriorsclerosis, kidney disease, retinopathy, and loss of peripheral nervous system sensitivity. Accordingly, a need exists to combine detection with measurement of glucose, glycosylated hemoglobin, HDL cholesterol, LDL cholesterol, and triglycerides.

8. c. 1. Background—High Density Lipoprotein (HDL) Testing

Measurement of high density lipoprotein cholesterol, particularly in conjunction with cholesterol measurement, has been proven to be an effective indicator of potential risk to arteriorsclerotic cardiovascular disease. Therefore, the determination of high density lipoprotein (HDL) cholesterol has become important and common in clinical laboratories.

The traditional method of measuring HDL cholesterol has been through wet chemistry tests that are time consuming and not well suited to home testing by patients.

For a measurement of high density lipoprotein cholesterol, it has heretofore been necessary to separate serum/plasma from whole blood by traditional methods of clotting or centrifugation. The separated plasma or serum was then added in a precise ratio with a precipitant system and mixed thoroughly to allow the completion of precipitate formation and agglomeration of the precipitated particles. The mixture was centrifuged to allow the precipitate to form a cake at the bottom of the centrifuge tube and the supernatant containing high density lipoprotein (HDL) was carefully withdrawn. The cholesterol associated with this HDL fraction (HDL cholesterol) was then measured either via wet chemistry. This was clearly not a patient friendly, home diagnostic test.

Another common method used for HDL cholesterol measurement is ultracentrifugation wherein various cholesterol-containing fractions are separated in an ultracentrifuge. This method is even more laborious and time consuming, requires considerable technical skill, and is quite expensive. Electrophoresis of lipoproteins has also been used but this again is slow, expensive and semi-quantitative. It is usually used only as an adjunct to other quantitative methods. Again, these methods are neither user friendly nor suited for home diagnostic testing.

HDL cholesterol measurements therefore tended to be time consuming with manual methods. These steps have been automated for clinical pathology laboratories with a large volume of sample throughput. The automated analyzers which can dispense and process the reagents automatically are available but can be quite complex and expensive.

One dry test method which is described in U.S. Pat. No. 5,135,716 to Thakore et al., is an assay using capillary action and a porous test strip containing sealed liquid reagents including visible indicators. This method takes advantage of the differential reactivity of HDL cholesterol versus cholesterol contained in other low and very low density lipoproteins (LDL and VLDL). This is said to eliminate the separation steps necessary for HDL cholesterol determination. The measurements are kinetic, meaning the rate of reaction of HDL cholesterol is monitored after LDL and VLDL cholesterol have all been reacted. This requires careful control of time and temperature. Precisely controlled volumes of reagents are added at precise times in a prescribed manner. Even though this presents a significant improvement, for accurate results, it needs careful operator supervision if done manually or expensive instrumentation if automated. While this method represents a step in the right direction, it is neither user friendly, nor inexpensive, nor adaptable to home diagnosis.

9. Background—Clotting Factors Clotting factors are frequently affected by drugs, especially in the case of hypercholesteric patients who are on anti-coagulant therapy. The measurement and control of clotting factors is especially critical for these factors. U.S. Pat. No. 5,059,525 to Bartl et al. Bartl et al. describe a dry test strip system for determination of clotting factors using an oxidizing agent, and an aniline or phenol derivative which forms a colored compound with a chromophoric protease substrate.

10. Background—Hemoglobin And "Iron"—Hemoglobin and its associated "iron" is an indicator for such serious conditions as toxicological pathologies, internal bleeding, and anemia. U.S. Pat. No. 4,017,261 to Svoboda et al., describes a try strip test for hemoglobin and iron. The systems uses a chromogen, a wetting agent, an agent capable of enhancing the peroxidase activity of hemoglobin, an organic hydroperoxide in the form of a stable, solid salt with an aliphatic, alicyclic or heterocyclic amine, and a solid, polymeric film forming material, all deposited on the test strip.

11. Background—Data Processing and Synchronization

It is desirable to integrate the periodic blood chemistry measurements in a single instrument, storing the results in a single database or set of databases for display and analysis. It is even more desirable to have the capability of uploading the data to a personal computer or server, and even to a health care provider.

This may be accomplished through the use of a simple processor in the measurement device, with the capability of having a simple database or spreadsheet, and the ability to upload or synchronize the blood chemistry data to a host computer.

Additionally, it is desirable to view and analyze the blood chemistry profile in conjunction with other clinical data, such as pulse rate, blood pressure, respiration, and electrocardiogram data.

SUMMARY OF THE INVENTION

A user friendly, home health care blood chemistry apparatus, method and system is provided. The invention requires only a "pin prick" sample (1 to 50 microliters) of capillary blood, eliminating the need for puncturing arteries and veins by a trained technician to obtain a blood sample. The sample is applied to a test strip including a sample receiving pad and sample analysis pads. The blood sample is applied to the sample receiving pad and flows, by surface tension, hydrophobicity, and capillary flow, to the separate analysis pads that are fluidically in parallel with each other and fluidically in series with the sample receiving pad. Each sample analysis pad contains reagents, including enzymes and dyes, that are specific to producing an optically detectable effect for a specific blood component. The optical effects are detected by a reflectance meter that is used in conjunction with the test strip. The optical effects are converted to digital data, and stored in a storage device associated with the meter, for transmission to a health care provider.

One aspect of the invention is a multi-component test strip for analyzing a plurality of blood components in a single blood sample. The test strip comprises a porous medium having a sample receiving region, and two or more sample analysis regions. The sample receiving region is fluidically in series with the two or more sample analysis regions, and the two or more sample analysis regions are fluidically in parallel with each other. The two or more sample analysis regions contain indicating reagents specific to two or more specific blood components.

The multi-component test strip includes an apertured first substrate, and an apertured second substrate, with the porous medium interposed between and bonded to the substrates and having the sample receiving region for receiving a blood sample in contact with the apertured first substrate and positioned to receive a blood sample through an aperture in the first substrate. The sample analysis regions are positioned with respect to the apertures in the second apertured substrate to display indications of the presence of blood components through the apertures in the second substrate.

The porous medium can have a sample receiving and distribution pad; and individual sample analysis pads. Alternatively, the porous medium may comprises a sample receiving pad; a sample distribution pad; and individual sample analysis pads; as where the sample distribution pad is positioned between the sample receiving pad and the individual sample analysis pads and is configured to divide sample from the sample receiving pad among the same analysis pads.

Alternatively, the test strip may contain a distributor between the first porous pad and the analysis pads for carrying portions of blood from the first porous pad and the analysis pads.

The apertured first substrate, the porous first pad, the distributor, the analysis pads, and the apertured second substrate are bonded together.

A further aspect of the invention is a method of collecting and recording blood component data. This method comprises depositing a blood sample on a test strip having two or more distinct regions for detecting and indicating the presence and concentration of blood fractions. The next step is measuring, digitizing, and storing indications of blood fraction concentration in an associated meter. The meter is configured to read blood fraction presence and concentration indications, digitize the indications, store the digitized indications, and transmit the digitized indications. The last step is transmitting the stored indications of blood fraction indication to a server.

The blood component data includes concentration of blood glucose and at least one other blood component, such as at least one other blood component that is chosen from the group consisting of glycosylated hemoglobin, cholesterol, LDL cholesterol, HDL cholesterol, triglycerides, hemoglobin, and clotting factors.

A further aspect of the invention is synchronizing the indications of blood fraction concentration on a local computer; and transmitting the synchronized indications of blood fraction from the local computer to a server.

A further aspect of the invention is a system configured to read a multi-indicator blood test strip, as described above with two or more distinct regions for detecting and colorimetrically indicating the presence and concentration of blood fractions. The system includes optics adapted to illuminate the distinct regions of the test strip and detect a colorimetric property (as color, optical absorption, and the like). The system further includes circuitry to digitize the detected colorimetric property for each of the regions; and memory circuitry to store the digitized colorimetric property of each of the regions. The system also has a display to display the digitized colorimetric properties of the regions; and input/output circuitry to receive commands from an associated computer and send digitized colorimetric properties of the regions to the associated computer.

The system is further characterized by having separate optics to illuminate and detect individual regions of the test strip. The input/output circuitry receives commands from an associated computer and sends digitized colorimetric properties of the regions to the associated computer, and contains, for example, synchronization circuitry and instructions to send the digitized colorimetric properties to an associated local computer, or, as an alternative, transmission circuitry and instructions to transmit the digitized colorimetric properties of the regions to a remote server, as over the internet.

A still further aspect of the invention is a method of and system for recording blood composition and cardiovascular measures. For example, a person could draw a blood sample upon rising, and take cardiovascular measures during exercise (as on a rowing machine, a stair climber, or a treadmill), record this information on one device, and upload it to a server. Thus an end user could monitor biological functions by analyzing a blood sample as described herein for concentrations of components thereof, and record the concentrations in an memory. The user could also measure and record cardiovascular measures in the associated memory. The recorded blood component concentrations and cardiovascular measures could then be uploaded to a remote server. The blood is analyzed as described herein, and includes blood component is selected from the group consisting of glucose, glycosylated hemoglobin, cholesterol, LDL cholesterol, HDL cholesterol, triglycerides, hemoglobin, and clotting factors. The cardiovascular measures are those measurable during exercise, and are chosen from the group consisting of blood pressure, respiration rate, and electrocardiogram. When the cardiovascular measure is an electrocardiogram reading, the electrocardiogram is compressed before transmission to the server.

THE FIGURES

Aspects of the invention are illustrated in the FIGURES appended hereto.

Figure 4:
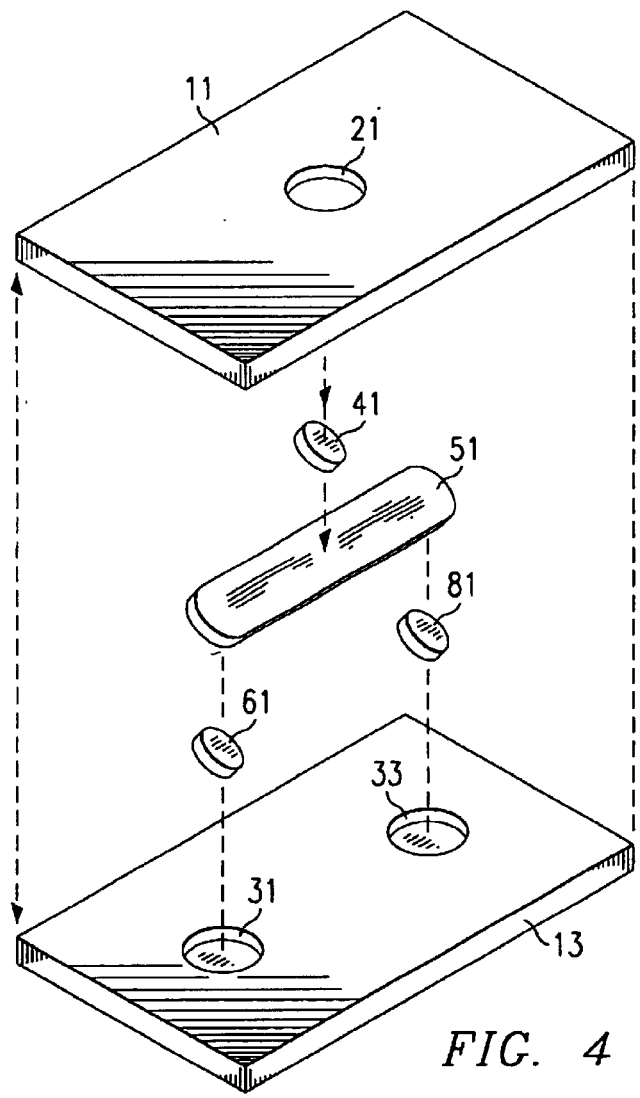

FIG. 4 is an exploded view of a test strip of the invention, showing a single apertured substrate for receiving a blood sample, a sample receiving pad, a distribution pad, two pads, typically containing one or more reagents, for optical indication of the blood component being analyzed for, and a multiple apertured substrate for measuring the change in optical property associated with an amount of the blood component being analyzed.

Figure 5:
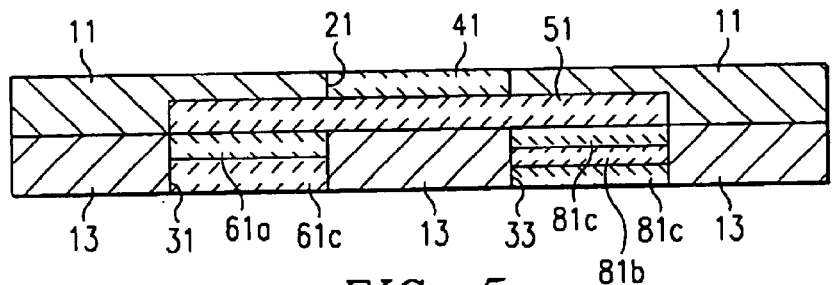

FIG. 5 is a cutaway view of a two component test strip of the invention, showing the single apertured substrate for receiving the blood sample, the sample receiving pad, the distribution pad, two pads, typically containing one or more reagents, for optical indication of the blood component being analyzed for, and the multiple apertured substrate for measuring the change in optical property associated with an amount of the blood component being analyzed.

Figure 6:
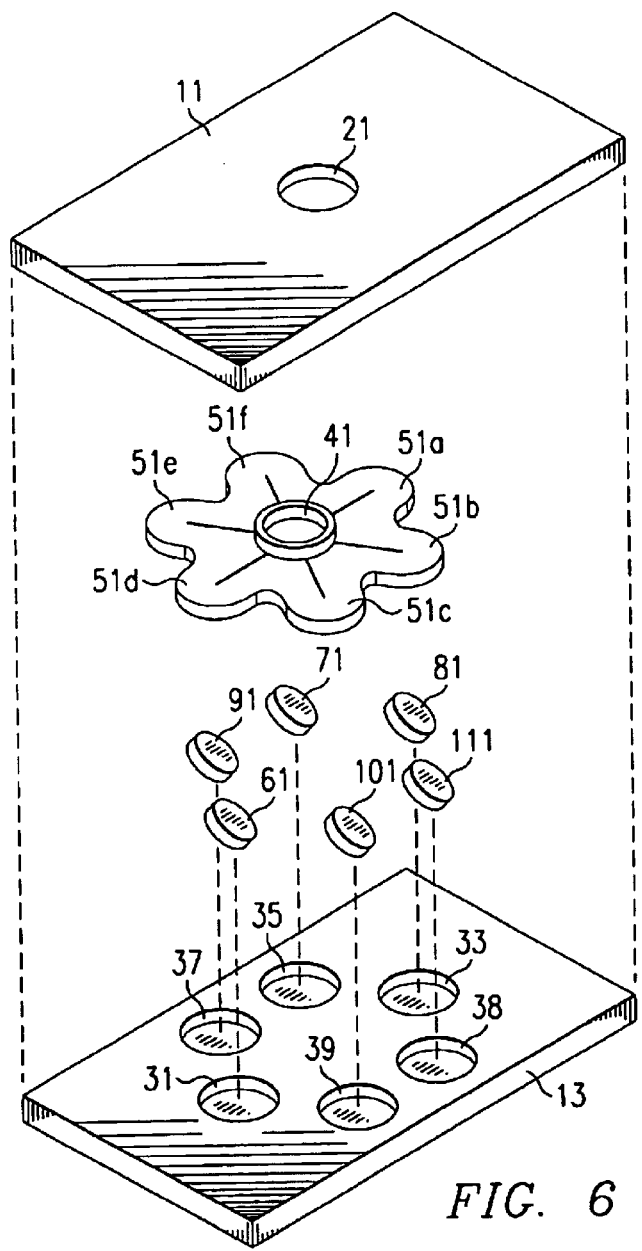

FIG. 6 is an exploded view of an alternative exemplification of a test strip of the invention for analyzing for six components. The view shows showing the single apertured substrate for receiving the blood sample, the sample receiving pad, the distribution pad, six pads, typically containing one or more reagents, for optical indication of the six blood component being analyzed for, and the multiple apertured substrate for measuring the change in optical property associated with an amount of the blood component being analyzed.

Figure 7:
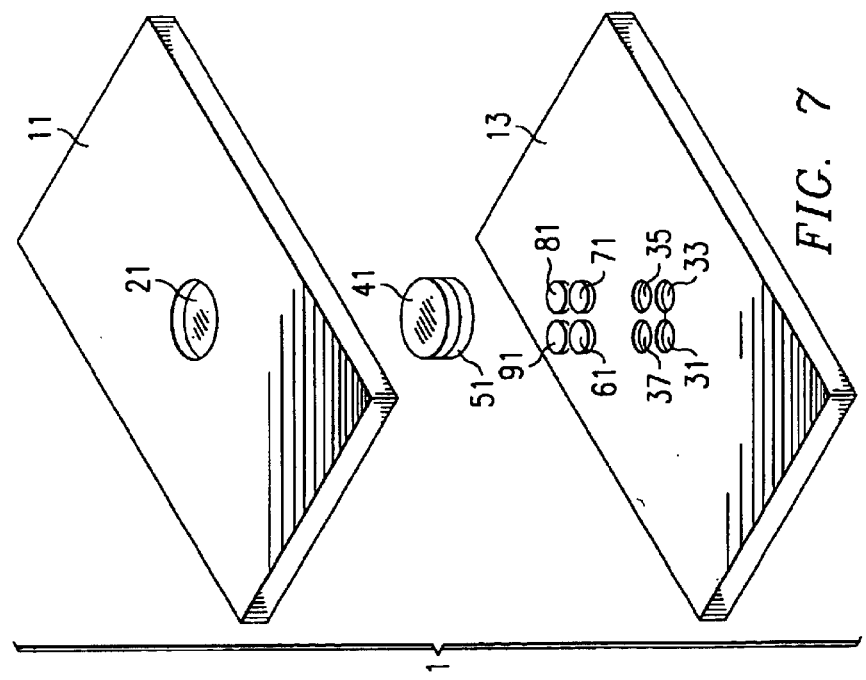

FIG. 7 is an exploded view of an alternative test strip of the invention where the sample receiving region and the sample distribution network are integrated with each other as a single element.

Figure 8:
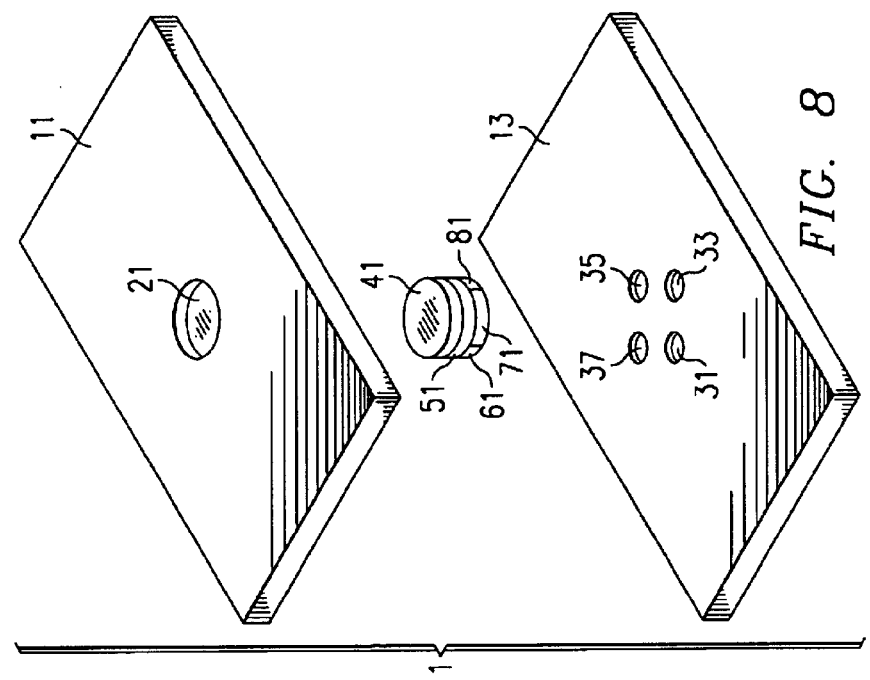

FIG. 8 is an exploded view of a still further alternative test strip of the invention where the sample receiving, the distribution network, and the individual analysis pads are integrated into a single unit, and where the sample analysis elements of the single, integrated pad may be prepared by syringe pumping small amounts of analytical reagents into selected volumes of the single element.

Figure 9:
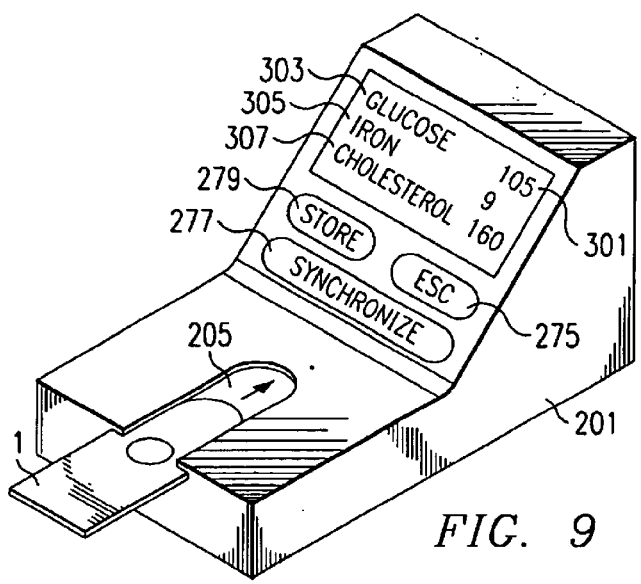

FIG. 9 is an isometric view of a tester of the invention. The tester has a slot for receiving the test strip, internal optics and logic, a display, and a keypad for user input.

Figure 10:
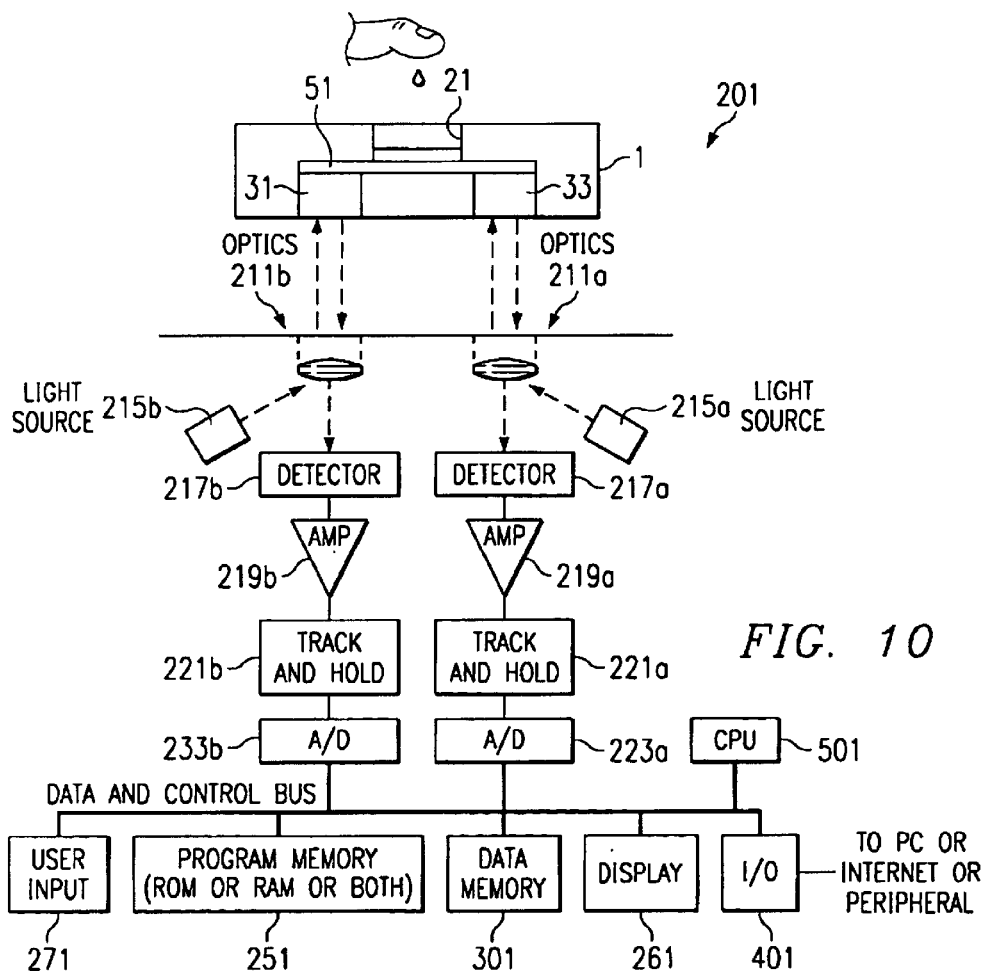

FIG. 10 is a circuit diagram of a tester of the type shown in FIG. 9, with a sample being shown to provide context, a test strip, optics and detectors for analysis of the individual analysis pads of the test strip, amplifiers, track and hold circuits, analog to digital converters, and a data and control bus. The data and control bus includes a provision for user input, program memory, data memory, display, and I/O. The I/O may provide input, output, and/or control to and/or from a network, a personal computer or work station, or a peripheral (such as an electrocardiograph, a blood pressure tester, a respiration meter, or a pulse meter, or a combination thereof).

Figure 11:
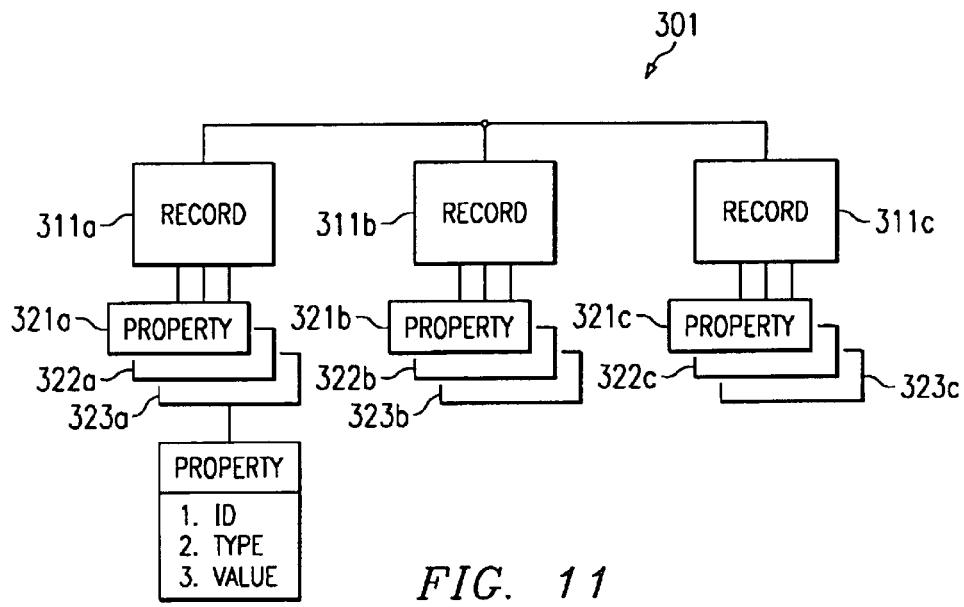

FIG. 11 shows the logical division of the database into records, the records into properties, and the enumeration of the properties.

Figure 12:
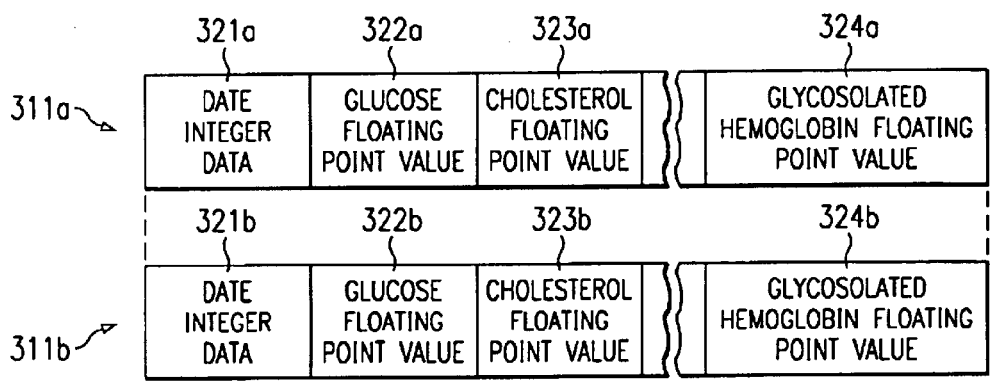

FIG. 12 is an illustration of the properties and attributes of a data record useful in the meter used in the practice of the invention.

Figure 13:
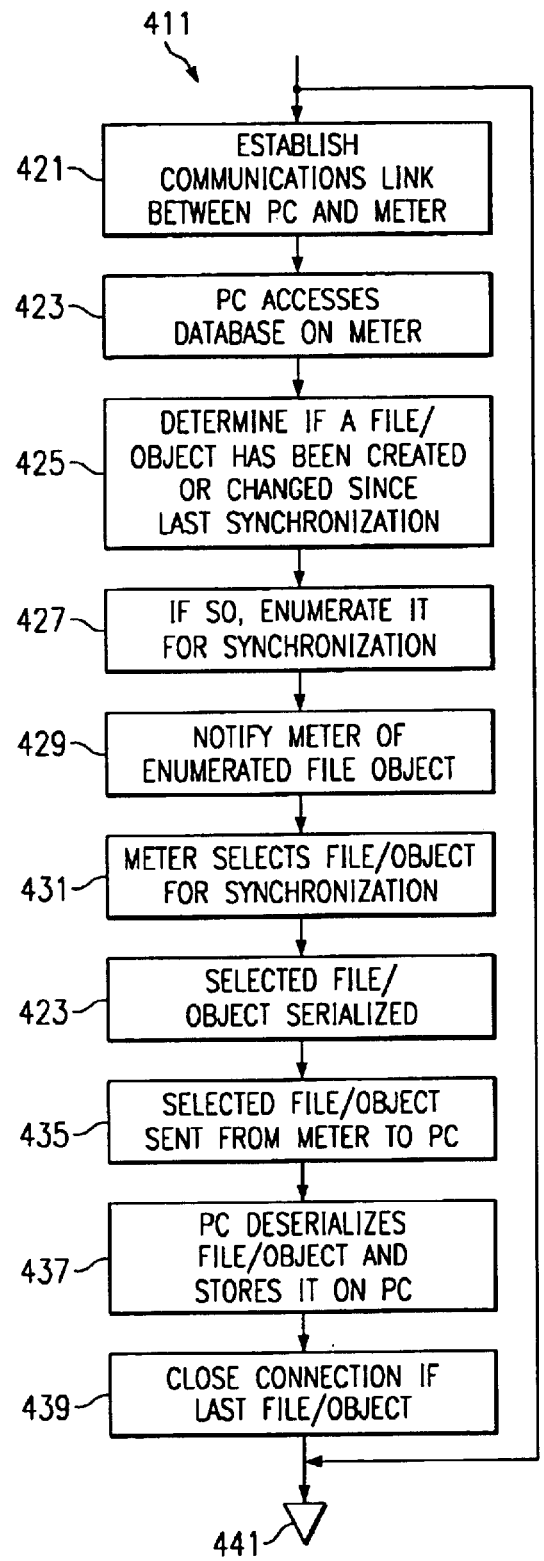

FIG. 13 illustrates a flow chart for one method of synchronizing a database in the tester with a database in an associated server.

Figure 14:
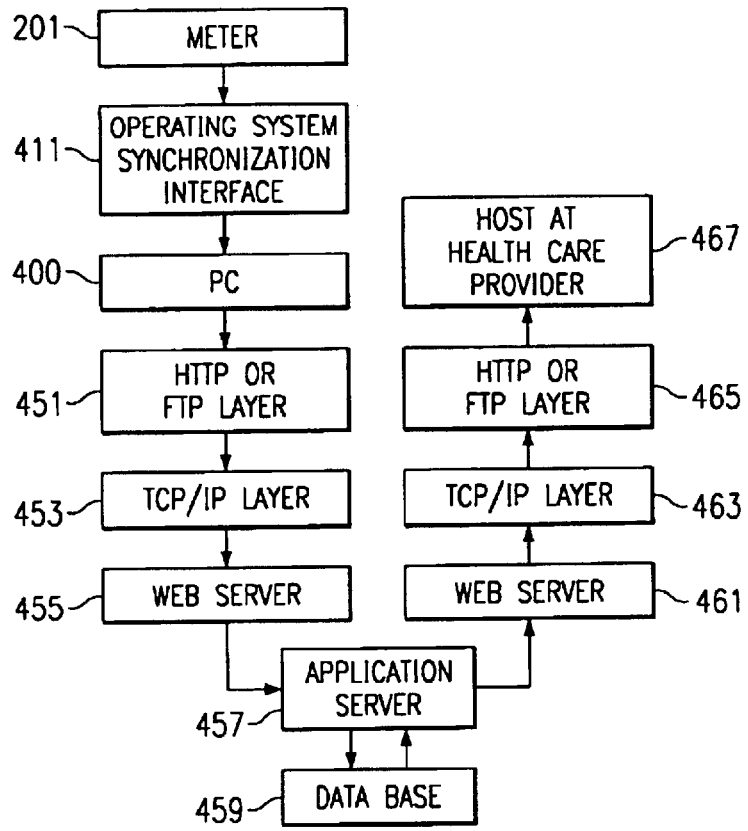

FIG. 14 illustrates logical layers between the meter and a host computer at the health care provider's site, using synchronization between the tester and a user's PC, and HTTP/TCP/IP layers between the user and the health care provider.

Figure 15:
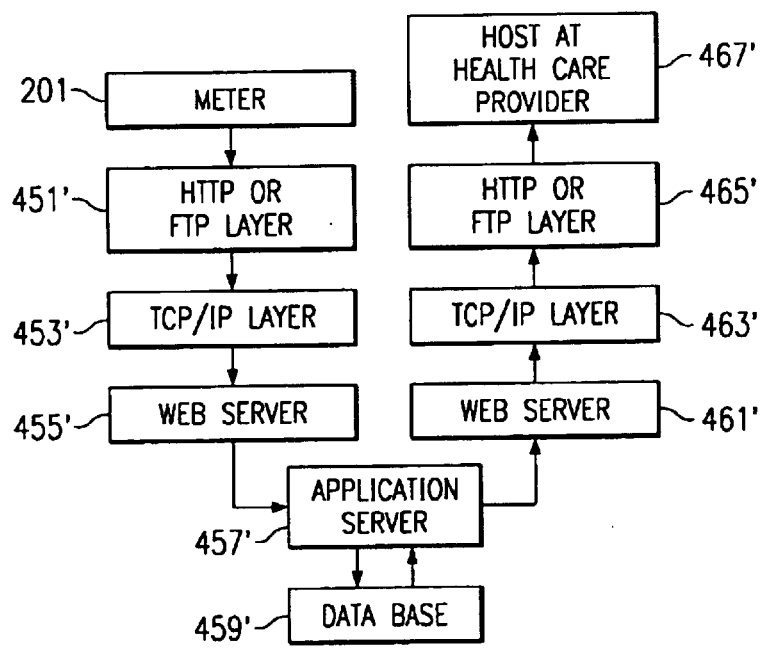

FIG. 15 illustrates logical layers between the meter and a host computer at the health care provider's site, using HTTP/TCP/IP layers between the user and the health care provider.

Figure 16:
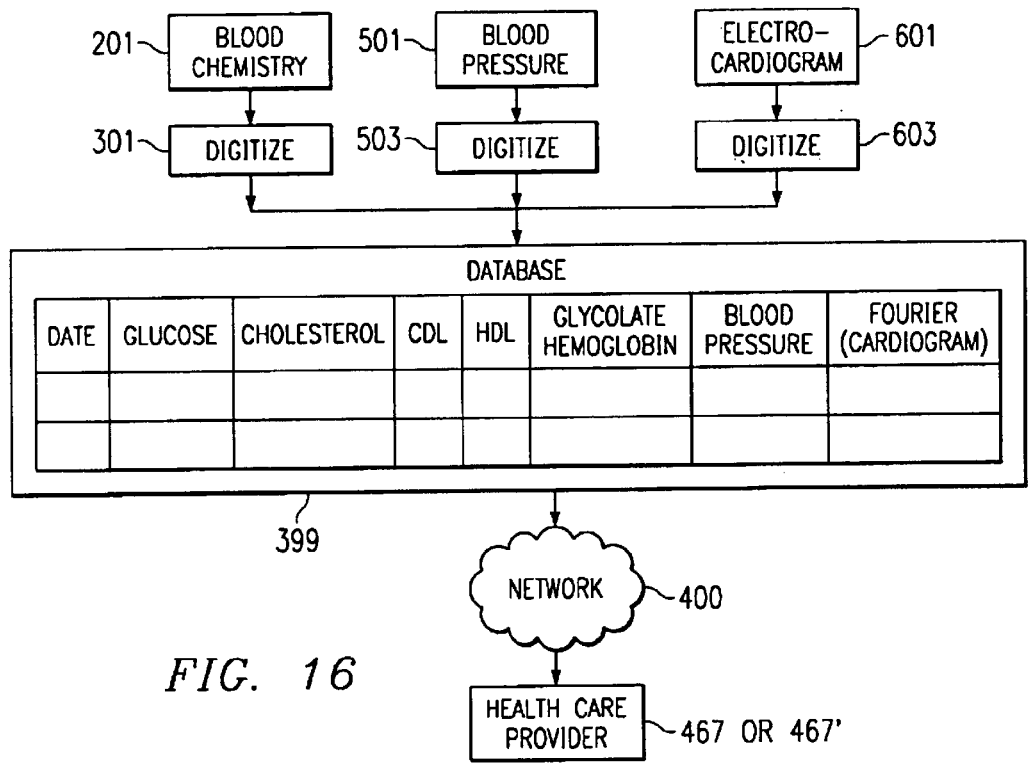

FIG. 16 illustrates logical layers and a database for an exemplification of the invention incorporating other medical data, as blood pressure and electrocardiogram data, into the report to the provider.

Figure 17:
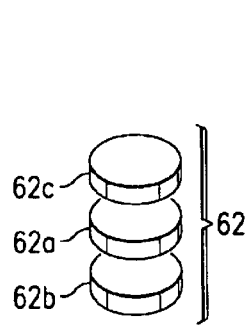

FIG. 17 is an exploded view of the test structure for glycosylated hemoglobin.

Figure 18:
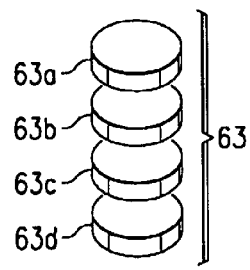

FIG. 18 is an exploded view of the test structure for LDL cholesterol.

Figure 19:
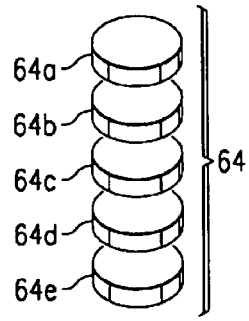

FIG. 19 is an exploded view of the test structure for HDL cholesterol.

OVERVIEW OF THE INVENTION

A user friendly, home health care blood chemistry apparatus, method and system is provided. The system, method, and apparatus provide a "basis" or "reference" for determining "trends" and "changes" that indicate the desirability of professional medical intervention, e.g., for analysis, sophisticated testing, and treatment. The system can also upload data to the health care provider, thereby allowing to provider to monitor a patient, and intervene where appropriate. The invention requires only a "pin prick" or "stick pin" sample (1 to 50 microliters) of capillary blood, eliminating the need for puncturing or invading arteries and veins by a trained technician to obtain a blood sample. The sample is applied to a test strip including a sample receiving pad and sample analysis pads. The blood sample is applied to the sample receiving pad and flows, by surface tension, hydrophobicity, and capillary flow, to the separate analysis pads that are fluidically in parallel with each other and fluidically in series with the sample receiving pad. Each sample analysis pad contains reagents, including enzymes and dyes, that are specific to producing an optically detectable effect for a specific blood component. The optical effects are detected by a reflectance meter that is used in conjunction with the test strip. The optical effects are converted to digital data, and stored in a storage device associated with the meter, for transmission to a health care provider.

Figure 1:
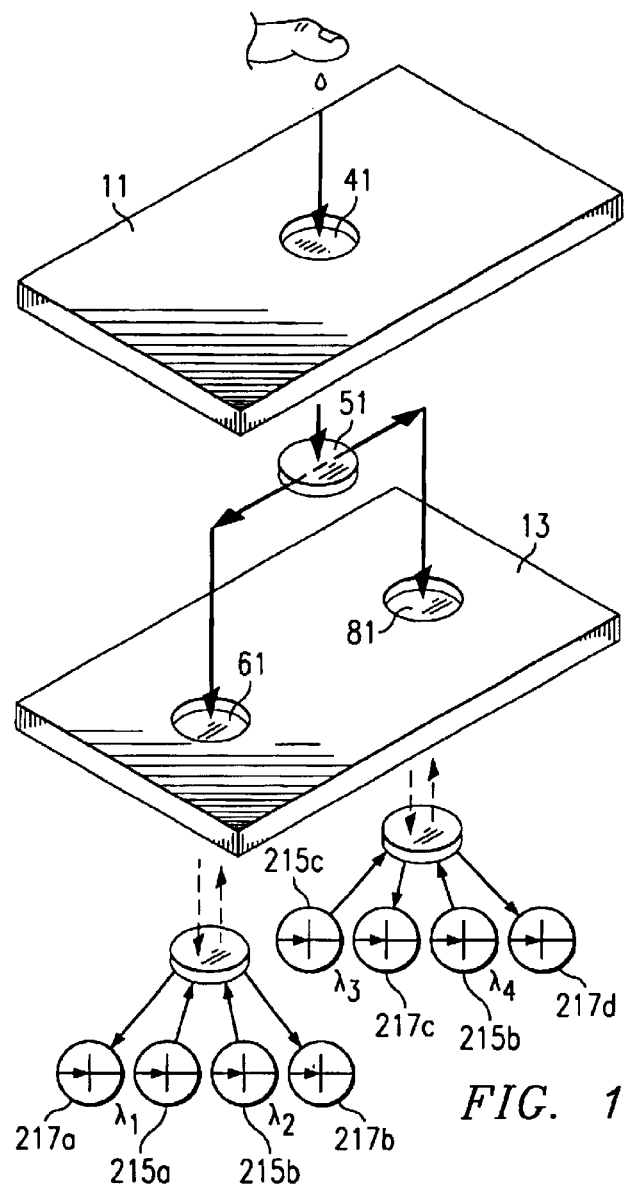
FIG. 1 is a high level overview of the system, method, and apparatus of the invention, showing the flow pattern of the blood sample in the test strip, the arrangement of the test pads in the test strip, and the optics of the associated meter.

FIG. 1 illustrates a very high level overview of the test strip of the invention, and its integration to the tester optics. Specifically, a sample of blood is shown falling to the sample receiving pad 41 in the top support 11 of the test strip 1. The blood travels, e.g., by hydrophobicity, surface tension, capillary flow, or the like to a distributor, distribution network, or divider 51 fluidically in series with the pad 41. Separated portions of the blood travel from the distributor, distribution network, or divider 51 to the analysis pads 61 and 81 that are fluidically in series with the distributor, distribution network, or divider 51 and fluidically in parallel with each other.

FIG. 1 further shows the reflectance switching optical systems, including light emitting diode-photo diode pairs 215a–217a at wavelength λ1 and 215b–217b at wavelength λ2, and also light emitting diode-photo diode pairs 215c–217c wavelength λ3 and 215d–217d at wavelength λ4, as will be described more fully hereinbelow.

To be noted, as shown in FIG. 7 and FIG. 8, is that the distribution network or divider 51 and the sample receiving element can be integrated into a single element (as shown in FIG. 7), and that the three elements, the sample receiving element 41 the sample distribution or dividing element 51, and the set of sample analysis elements, 61, 71, 81, 91, can be selected regions of the same integral element.

Figure 2:
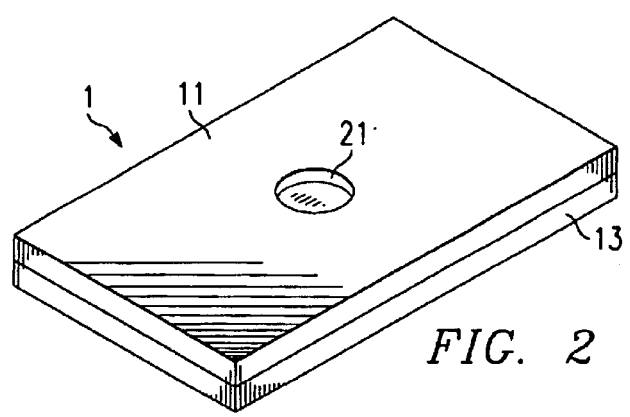
FIG. 2 is an isometric view of the sample receiving surface of a test strip of the invention.
Figure 3:
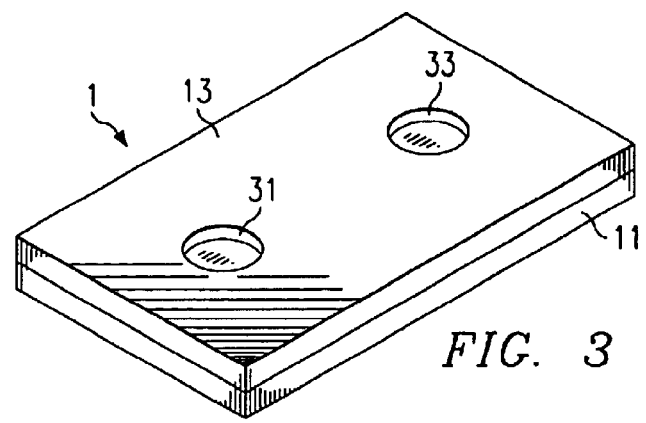
FIG. 3 is an isometric view of the sample analyzing surface of a test strip of the invention, showing analysis apertures for a two component analysis.

FIGS. 2 and 3 are isometric views of the test strip 1 of the invention, with FIG. 2 being an isometric view of the sample receiving surface of a test strip 1 of the invention, and FIG. 3 being an isometric view of the sample analyzing surface of a test strip 1 of the invention, showing analysis apertures for a two component analysis.

FIG. 4 is an exploded view of a test strip 1 of the invention, showing a single apertured 21 substrate 11 for receiving a blood sample, a sample receiving pad, 41, a sample division or distribution pad or network, 51, two pads, 61,81, typically containing one or more reagents, for optical indication of the blood component being analyzed for, and a multiple apertured, 31,33, substrate, 13, for measuring the change in optical property associated with an amount of the blood component being analyzed.

The sample analysis pads or elements 61,81, are fluidically in parallel with each other, and fluidically in series with the sample receiving pad 41, for example, through the sample distribution division element or network, 51.

FIG. 5 is a cutaway view of a two component test strip, 1, of the invention, showing the single apertured, 21, substrate, 11, for receiving the blood sample, the sample receiving pad, element, or region, 41, the sample division or distribution pad, network, or element, 51, two pads, 61, 81, typically containing one or more reagents, for optical indication of the blood component being analyzed for, and the multiple apertured substrate for measuring the change in optical property associated with an amount of the blood component being analyzed.

FIG. 6 is an exploded view of an alternative exemplification of a test strip, 1, of the invention for analyzing for six components. The view shows the single apertured, 21, substrate, 11, for receiving the blood sample, the sample receiving pad, 41, the distribution pad or network, 51, six pads, 61, 71, 81, 91, 101, and 111, typically containing one or more reagents, for optical indication of the six blood component being analyzed for, and the multiple apertured, 31, 33, 35, 37, 39, and 41, substrate, 13, for measuring the change in optical property associated with an amount of the blood component being analyzed.

Turning now to FIG. 7 and FIG. 8, to be noted is that the distribution network or divider 51 and the sample receiving element can be integrated into a single element (as shown in FIG. 7), and that the three elements, the sample receiving element 41 the sample distribution or dividing element 51, and the set of sample analysis elements, 61, 71, 81, 91, can be selected regions of the same integral element (as shown in FIG. 8).

FIG. 9 is an isometric view of a tester, 201, of the invention. The tester, 201, has a slot, 205, for receiving the test strip, 1, internal optics and logic, a display, 301, and a keypad, 275, 277, and 279, for user input.

FIG. 10 is a circuit diagram of a tester of the type shown in FIG. 9, with a sample being shown to provide context, a test strip, 1, optics, 211a, 211b, and detectors, 217a, 217b, for analysis of the individual analysis pads, 31, 33, of the test strip, amplifiers, 219a, 219b, track and hold circuits, 221a, 221b, analog to digital converters, 233a, 233b, and a data and control bus. The data and control bus includes a provision for user input, 271, program memory, 251, data memory, 301, display, 261, and I/O, 401. The input/output, 401, provides connectivity, e.g., for data and/or control, to a host computer, a network and to peripherals, such as an electrocardiograph (preferably with self contained data compression), a blood pressure cuff, a pulse measurement device, and a respiration device.

FIG. 11 shows the logical division of the database, 301, into records, 311a, 311b, 311c, the records, 311a, 311b, 311c, into properties, 321a, 322a, 323a, 321b, 322b, 323b, 321c, 322c, and 323c, and the enumeration of the properties. FIG. 12 is an illustration of the properties 321 and attributes 311 of a data record useful in the meter used in the practice of the invention.

The flow chart and logical layers for data communication and synchronization are illustrated in FIG. 13, FIG. 14, and FIG. 15. FIG. 13 illustrates a flow chart for one method of synchronizing a database in the tester with a database in an associated server. FIG. 14 illustrates logical layers between the meter and a host computer at the health care provider's site, using synchronization between the tester and a user's PC, and HTTP/TCP/IP layers between the user and the health care provider. FIG. 15 illustrates logical layers between the meter and a host computer at the health care provider's site, using HTTP/TCP/IP layers between the user and the health care provider.

FIG. 16 illustrates logical layers and a database for an exemplification of the invention incorporating other medical data, as blood pressure and electrocardiogram data, into the report to the provider.

DETAILED DESCRIPTION OF THE INVENTION

A user friendly, home health care blood chemistry apparatus, method and system is provided. The invention requires only a "pin prick" or "pin stick" sample (1 to 50 microliters) of capillary blood, eliminating the need for puncturing arteries and veins by a trained technician to obtain a blood sample. Preferably the wound is self healing, not requiring a bandage or dressing. The sample is applied to a test strip, 1, including a sample receiving pad or region, 41, and sample analysis pads, 61, 81. The blood sample is applied to the sample receiving pad and flows, by surface tension, hydrophobicity, and capillary flow, to the separate analysis pads that are fluidically in parallel with each other and fluidically in series with the sample receiving pad. The blood sample is divided and distributed from the sample receiving pad, or region, 41, to the sample analysis pads or regions 61, 81, either through a separate sample distribution or dividing network, 51, or through a combined, integral network element integral with either or both of the sample receiving pad, element, or region, 41, or the sample analysis pad, element, or region, 61, 81. Each sample analysis pad contains reagents, including enzymes and dyes, that are specific to producing an optically detectable effect for a specific blood component. The optical effects are detected by a reflectance meter, 201, that is used in conjunction with the test strip, 1. The optical effects are converted to digital data, and stored in a storage device associated with the meter, for example, for future reference and analysis or for transmission to a health care provider.

The integrated user friendly blood profile system, method, and apparatus contains two associated components. One is a multi-component test strip, 1. The other element is an associated, integrated analyzer, 201, for use with the multi-component test strip, 1.

The test strip, 1, has a sample receiving region, pad, or mat, 41, and a plurality of separate sample analysis regions (absorbent pads or mats with indicator reagents therein), 61, 81, one for each blood fraction or component being quantified. Each region is a unique lamination of porous and microporous sheets, plies, and layers, some carrying immobilized enzymes, dyes, or reagents to quantify a specific blood fraction. The sample receiving region, pad, or mat, 41, is fluidically in series with each of the sample analysis regions, pads, or mats, 61, 81, and all of the sample analysis regions, pads, or mats 61, 81, are fluidically in parallel with each other. The regions are joined to the sample receiving region by a porous, microporous, or capillary flow region in the form of a distributor or manifold, 51, which may a separate and distinct structure, pad, or mat, or be incorporated into the sample receiving pad, mat, or structure, 41, or the sample analysis structures, 61, 81. A small sample of blood is placed on the sample receiving region. The blood moves, through the system of porous, microporous, and capillary flow regions of the distributor or manifold to the separate analysis regions, pads, or mats for analysis. There are separate analysis apertures on the bottom surface of the test strip for colorimetric analysis of each fraction.

The colorimetric analysis is carried out by a spectrophotometer or colorimeter shown in FIG. 10. The spectrophotometer measures an optical property of each sample region, processes it, and stores it in memory for future analysis.

1. Glucose Determinations 1. a. Glucose Determinations—General. The test zone, region, mat, or pad of the sample strip used for quantitatively determining glucose reacts the glucose with a suitable immobilized enzyme. This reaction initiates a series of reactions resulting in a measurable color change which is correlated with the glucose content of the blood sample. The color change is measured and processed.

The glucose analysis region, pad, or mat of the test strips has a hydrophilic porous matrix containing a "signal producing system" (immobilized enzymes and dyes that support a colorimetric chemical reaction sequence yielding a detectable color, reflectivity, or optical absorbency change that can be correlated with the glucose content of the analyte). The test strip is used in combination with an associated reflectance, absorbance, or color measuring apparatus which is activated upon a change in reflectance, absorbance, or color of the hydrophilic porous matrix when analyte penetrates the matrix. The method begins when a sample whole blood is placed on an exposed surface of the sample receiving hydrophilic matrix, and flows through the distributor or matrix to the individual glucose analysis hydrophilic matrix, pad, or mat. The matrix performs a "rough cut" separation or fractionation or chromatographic separation of the blood, filtering out large particles, such as red blood cells, and passing the glucose-containing plasma. As the glucose-containing plasma passes through the matrix, the entrained and immobilized enzymes and reagents therein, that is, the "signal-producing system", produces a blood reaction product which further changes the reflectance of the matrix. This change can be related to the (quantitative) presence of a blood glucose in the sample.

For measuring glucose in blood, whole blood is typically used as the assay medium. The porous matrix contains an immobilized oxidase enzyme which produces hydrogen peroxide from the glucose. The matrix also contains a second immobilized enzyme, particularly a peroxidase, and a dye system which produces a light-absorbing product in conjunction with the peroxidase. The light-absorbing enzyme reaction product changes the reflectance of the matrix system. Preferably, whole blood, readings are taken at two different wavelengths, with the reading at one wavelength used to subtract out background interference caused by hematocrit, blood oxygenation, and other variables which may affect the result.

In use, the blood sample being analyzed is applied to one side of a test strip or sheet so that the blood passes through the matrix/immobilized enzyme element by capillary action, wicking, gravity flow and/or diffusion actions. The components of the signal producing chemical/immobilized enzyme system present in the matrix react with the glucose to give a light absorbing reaction product. Incident light impinges upon the matrix at a different location than the location to which the sample was applied (i.e., after the blood has wicked through the matrix and reacted with the immobilized enzyme. Light is reflected from the surface of the element as diffuse reflected light.

This diffuse light is collected and measured, for example by the detector of a reflectance spectrophotometer. The amount of reflected light will be related to the amount of blood fraction in the sample, usually being an inverse function of the amount of blood fraction in the sample.

Each of the components necessary for producing the reagent element will be described in turn. The first component is the matrix itself.

1. a. Glucose Determinations—Mat or Pad The matrix is a hydrophilic porous matrix to which reagents (immobilized enzymes and dyes) may be covalently or noncovalently bound. The matrix allows for the flow of an aqueous medium (e.g., blood) through the matrix. It also allows for binding of protein compositions to the matrix without significantly adversely affecting the biological activity of the protein, e.g., the enzymatic activity of an enzyme. The composition of the matrix is reflective and the matrix is of sufficient thickness to permit the formation of light-absorbing dye in the void volume of the matrix or on the internal (pore) surfaces of the matrix to substantially affect the reflectance from the matrix. The matrix may be of a uniform composition or a coating on a substrate providing the necessary structure and physical properties.

The matrix should not deform on wetting, thus retaining its original conformation and size. The matrix will have a defined absorbance, so that the glucose volume which is absorbed can be calibrated within reasonable limits. In the case of an absorbent matrix, the matrix has sufficient wet strength to allow for routine manufacture. The matrix permits non-covalently bound reagents to be relatively uniformly distributed on the surface of the matrix.

Exemplary of fibrous matrix surfaces are polyamides, particularly with samples involving whole blood. The polyamides are conveniently condensation polymers of monomers of from 4 to 8 carbon atoms, where the monomers are lactams or combinations of diamines and di-carboxylic acids. Other polymeric compositions having comparable properties may also be used. The polyamide compositions may be modified to introduce other functional groups which provide for charged structures, so that the surfaces of the matrix may be neutral, positive or negative, as well as neutral, basic or acidic. Preferred surfaces are positively charged. Experiences of others in the field demonstrate that positive charge on the matrix enhances both stability and shelf-life.

When used with whole blood, the porous matrix preferably has pores with an average diameter in the range of from about 0.1 to 2.0 $\mu$m, more preferably from about 0.6 to 1.0 $\mu$m. When the porous matrix contains pores having an average diameter of about 0.8 $\mu$m, the sample of blood will not cause a chromatographic effect. That is, the blood sample will not seek out the edges of a circular matrix. Rather, the blood remains seated within all the pores of the matrix and provides for a uniform readability of the entire matrix. In addition, this pore size maximizes the non-blotting effect of the blood. That is, the pore size is both adequately filled, but not overfilled, so that the hematocrit level of blood will not cause the sample to require blotting prior to reading of the sample. Also, it has been reported that pores of this size are optimal when shelf-life and stability are taken into consideration.

A preferred manner of preparing the fibrous porous material is to cast the hydrophilic polymer onto a core of non-woven fibers. The core fibers can be any fibrous material that produce the described integrity and strength, such as polyesters and polyamides. The reagent that will form the light-absorbing reaction product, which is discussed later in detail, is present within the pores of the matrix but does not block the matrix so that the liquid portion of the blood, being analyzed can flow through the pores of the matrix, while particles, such as erythrocytes, are held at the surface.

The matrix is substantially reflective so that it gives a diffuse reflectance without the use of a reflective backing. Preferably at least 25%, and more preferably at least 50%, of the incident light applied to the matrix is reflected and emitted as diffuse reflectance. A fibrous matrix of less than about 0.5 mm thickness is preferred, with a thickness of from about 0.01 mm to about 0.3 mm being particularly preferred, and a thickness of from about 0.1 mm to about 0.2 mm being most preferred, particularly for a nylon matrix.

Typically, the matrix will be attached to the test strip in order to give it physical form and rigidity, although this may not be necessary. In most user friendly glucose meters, there is a strip having a thin hydrophilic matrix pad is positioned at one end of a plastic holder or handle or insert.

Generally, with blood being tested, the reagent pad or hydrophilic matrix will be on the order of about 10 mm$^2$ to 100 mm$^2$ in surface area, especially 10 mm$^2$ to 50 mm$^2$ in area (or having a diameter of about 2 mm to about 10 mm). This is a volume that 5–10 microliters of sample will more than saturate. To be noted is that several different blood components may be analyzed for in discrete regions of the analysis pads, 61, 81, with unique chemistries in the selected regions.

1. c. Glucose Determinations—Chemistry. Any signal producing immobilized enzyme and dye system may be employed that is capable of reacting with the glucose in the sample to produce (either directly or indirectly) a compound that is reproducibly quantitatively absorptive at a wavelength other than a wavelength at which the assay medium substantially absorbs incident light.

In the case of fibrous matrices, polyamide matrices are particularly useful for carrying out reactions in which a substrate (glucose) reacts with an oxygen-utilizing oxidase enzyme so that an intermediate reaction product is produced. This intermediate reaction product further reacts with a dye intermediate to either directly or indirectly form a dye which absorbs in a predetermined wavelength range. For example, an oxidase enzyme can oxidize a glucose substrate and produce hydrogen peroxide as an intermediate reaction product. The hydrogen peroxide can then react with a dye intermediate or precursor, in a catalyzed or uncatalyzed reaction, to produce an oxidized form of the intermediate or precursor. This oxidized material may produce the colored product or react with a second precursor to form the final dye. This is shown in equations (1) and (2)

Glucose+Oxidase→Hydrogen Peroxide (3)

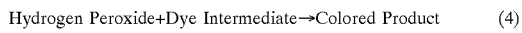

Hydrogen Peroxide+Dye Intermediate→Colored Product (4)

Typical immobilized enzymes include Glucose Oxidase, Glucose Peroxidase for glucose.

Any signal producing enzyme-dye chemistry system may be employed that is capable of reacting with the blood glucose in the sample to produce (either directly or indirectly) a compound that is absorptive at a wavelength other than a wavelength at which the matrix and blood substantially absorb.

The enzyme-dye system is deposited in a porous matrix. Desirable results can be obtained with pore sizes ranging from about 0.2–2.0 μm, preferably about 0.5–1.2 μm, and most preferably about 0.8 μm, when used with whole blood. Polyamide matrices are particularly useful for carrying out reactions in which glucose reacts with an oxygen-utilizing oxidase enzyme in such a manner that a product is produced that further reacts with a dye or dye intermediate to either directly or indirectly form a dye which absorbs in a predetermined wavelength range. For example, an oxidase enzyme oxidizes glucose and produce hydrogen peroxide as a reaction product. The hydrogen peroxide then reacts with a dye intermediate or precursor to produce an oxidized form of the dye intermediate or precursor. This oxidized material may be the colored product ("signal") or it may react with a second precursor to form the final dye.

The enzyme may be either glucose oxidase, or glucose peroxidase. The enzyme is present with an oxygen acceptor. Oxygen acceptors include O-dianisidine, O-toluidine, O-tolidine, Benzidine, 2,2'-Azinodi-(3-ethylbenzthiazoline sulphonic acid), 3-Methyl-2-benzothiazolinone hydrazone plus N,N-dimethylaniline, Phenol plus 4-aminophenazone, Sulfonated 2,4-dichlorophenol plus 4-aminophenazone(2), 3-Methyl-2-benzothiazolinone hydrazone plus 3-(dimethylamino)benzoicacid, 2-Methoxy-4-allyl phenol, and 4-Aminoantipyrinedimethylaniline.

Although a number of dyes could be used as indicators, it is necessary to select a dye having an absorbance at a wavelength different from the wavelength at which red blood cells, whole blood, the analysis pad, and contaminants absorb light. One suitable dye is the MBTH-DMAB dye couple (3-methyl-2-benzothiazolinone hydrazone hydrochloride and 3-dimethylaminobenzoic acid). Another dye couple that can be used in the measurement of glucose is the AAP-CTA (4-aminoantipyrene and chromotropic acid) couple.

The dye, i.e., MBTH-DMAB or AAP-CTA, forms a chromophore that absorbs at approximately 635 nm but not to any significant extent at 700 nm. At 700 nm both hematocrit and degree of oxygenation can be measured by measuring blood color. Furthermore, light emitting diodes (LED) are commercially available for both 635 nm and 700 nm measurements, thereby simplifying mass-production of a device.

1. c. Glucose Determinations—Method and System. The analysis method for glucose relies on a change in optical absorbance, as measured by diffuse reflectance. The diffuse is dependent upon the amount of glucose present in the sample being tested. The glucose concentration may be determined by measuring the change in the absorbance of the test sample between two or more points in time.

The first step of the analysis is the application of the blood sample to the matrix. In practice, an analysis could be carried out as follows: First a sample of blood containing glucose is obtained. The glucose in the blood reacts with immobilized enzymes in the matrix to effect a color change. The test strip is mounted in the meter for reading light absorbance, e.g., color intensity by reflectance, prior to application of the blood sample. Light absorbance is measured at certain selected points in time after application of the blood sample. Light absorbance refers not only to light within the visual wavelength range but also outside the visual wavelength range, such as infrared and ultraviolet radiation. From these measurements of light absorbance, degree of color development can be calibrated in terms of glucose level.

The measurement instrument, such as a diffuse reflectance spectrophotometer with appropriate software, automatically reads reflectance at certain selected points in time, calculates the rate of reflectance change, and, using calibration factors, outputs the level of glucose in the blood. A blood glucose meter with a spectrophotometer has a structure for holding the matrix in proximity to a light source. The light source, which may be, for example, a high intensity light emitting diode (LED), a laser, a vapor bulb, or an incandescent bulb, projects a beam of light onto the sample and enzyme product containing region of the porous matrix. A substantial portion (at least 25%, preferably at least 35%, and more preferably at least 50%, in the absence of reaction product) of this light is diffusively reflected from the porous matrix, and is detected by a light detector. The light detector can be, for example, a phototransistor that produces an output current proportional to the light it receives.

The light source and/or the detector can be adapted to generate or respond to a particular wavelength light, if desired. In many systems, two wave lengths of light are used, 635 nm and 700 nm. This is because the chromophore produced by the glucose-enzyme reactions, and the subsequent reaction with the dye, has different optical characteristics at 635 nm and 700 nm.

2. Glycosylated Hemoglobin Determinations

An indirect method of analysis may be used for glycosylated hemoglobin testing by analysis for fructosamine. Fructosamines are formed by glycosylated proteins. Glucose binds to an amino group of the protein to form a Schiff base, i.e., a glycosylamine or aldimine, that undergoes molecular rearrangement to form a stable ketoamine. In the art, such ketoamines are generically known as "fructosamines." Since fructosamine formation is directly dependent upon glucose concentration, diabetic individuals have higher fructosamine concentrations in the blood as compared to non-diabetic individuals. Under alkaline conditions, the fructosamines that form in the blood are converted to eneaminols. The eneaminol form of fructosamine is a chemically active reducing substance that reacts with a suitable indicator capable of being reduced by fructosamine. For example, the color transition of a chromogenic dye or the fluorescence of a fluorescent reagent resulting from this reaction can be measured and compared with a standard to give an indication of the average glucose concentration in blood samples over the prior half month period. In general, the fructosamine concentration in a blood, such as blood serum, reflects an average glucose concentration over a period of approximately a half month.

Glycosolated hemoglobin concentration can be indirectly determined using a multi-layer, porous matrix 21, shown in FIGS. 1, 2, and 6, similar to the matrix described above for glucose.

The Multi-Layers: The layers, 62a, 62b, of the multi-layer fructosamine test element, 62, shown in partial exploded view in FIG. 17, are positioned adjacent or atop each other so that they provide for fluid communication between the matrices. The fluid flow between the horizontally or vertically adjacent layers can be either vertical or horizontal. Accordingly, the layers of the multi-layer device can be superposed or juxtaposed.

The various multi-layers, 62a, 62b, of the test element, 62, contain the appropriate assay reagents, such as a buffer or an indicator. The reagents are impregnated into the layer or coated into or onto a layer or covalently attached to the layer, for example to the internal pores, interstices, and capillaries of the layer.

The material for the various layers, including the buffer layer, 62a, the indicator layer 62b, and any additional layers, comprise a porous matrix which is capable of containing the reagents and enzymes but which is permeable to the fructosamine blood fraction and other reagents and liquids. The permeability generally arises from porosity, the ability to swell or any other characteristic. The test element layers, 62a, 62b, can be formed of various porous, fibrous materials such as cellulose, papers, fleeces, felts, woven fabric and the like. Alternatively, the test strip layers can contain porous, non-fibrous materials, such as microporous polymers. Specific examples of suitable materials which can be used for the layers include filter paper, such as 3 mm filter paper.

The multiple layers, 62a, 62b, of the test element, 62, contain enzymes and reagents, such as a buffer or indicator, and can be loaded and assembled simultaneously or sequentially. The porous material for a given layer is first placed in a solution of assay reagent such as a buffer solution or an indicator solution. After drying, the layer can be stored in a desiccator cabinet until it is ready for lamination into the multi-layer test strip.

The multi-layers, 62a, 62b, are generally in the form of individual reagent pads which are mounted onto one support member or sandwiched between two or more support members as discussed more fully below. The individual multi-layer pads can be any geometrical dimension, such as circular or rectangular, and are generally 0.5 to 10 mm in circumference, preferably 1 to 5 mm, and are positioned either superposed or juxtaposed relative to each other.

Regardless of the multi-layer positioning, the test devices which can be used to quantitatively analyze for fructosamine comprise the basic elements of a buffer layer, an indicator layer and can contain additional layers as described below.

Buffer Layer: The buffer layer 62a contains a buffer having a pH value of at least 9. Various known types of buffers can be contained in the buffer layer as long as the buffer provides sufficiently high pH such that the fructosamines are converted to their eneaminol form. To achieve this, the pH of the buffer should be at a pH value between about 9 and about 13, and for optimum results the pH is at a pH value of between 10 and 12. Examples of such buffers include potassium hydrogen phosphate, sodium hydrogen phosphate, sodium hydroxide, guanidinium salts, certain amino acids, and other suitable buffers as are well known, or combinations thereof. Where the buffer layer is superposed above the indicator layer it is generally of a non-opaque, liquid-permeable material.

Indicator Layer: The indicator layer, 62b, contains any indicator capable of being reduced by fructosamine such as certain dyes, including chromogenic dyes, or fluorescent reagents. Examples of suitable chromogenic dyes which change color based on the amount of fructosamine present in a liquid sample include tetrazolium dyes such as Neotetrazolium chloride (NT), Tetranitroblue tetrazolium chloride (TNBT), Blue tetrazolium chloride (BT), Iodonitrotetrazolium chloride, Nitroblue tetrazolium chloride (NBT), Nitro Blue Monotetrazolium Chloride, Thiazolyl blue tetrazolium bromide (MTT), Tetrazolium violet, 2,3,5-Triphenyl-2-H-tetrazolium chloride, Thiocarbamyl nitro blue tetrazolium chloride (TCNBT), Tetrazolium XTT (XTT), 2-2'-Benzothiazolyl-5-styryl-3-(4'-phthalhydrazidyl) tetrazolium chloride (BSPT), Distyryl nitroblue tetrazolium chloride (DSNBT). An example of a suitable fluorescent reagents is 5-Cyano-2,3-ditolyl tetrazolium chloride (CTC).

Additional Layers: Other layers, in addition to the buffer layer and the indicator layer, can be used in the fructosamine test device. For example, the multi-layer test device can include a red blood cell (RBC) separation layer or layers before the buffer layer pad, for the purpose of separating RBC components. Other useful layers, include, but are not limited to radiation blocking layers, interference removal layers which can contain detergents, chelators, antioxidants, or other substances which can interfere with accurate results, contamination prevention layers, dialysis layers, filtering layers, support layers and the like.

3. Lipid Determinations Lipid determinations include the determination of one or more of cholesterol, LDL cholesterol, HDL, cholesterol, and triglycerides.

3. a. Cholesterol Determinations

U.S. Pat. No. 5,912,139 to Iwata describes a dry test for cholesterol. According to Iwata, an insert for dry test strip detection and measurement of cholesterol has been achieved by providing a test strip which comprises a carrier, a dehydrogenase (cholesterol dehydrogenase), diaphorase, a fluorescent chromogen and nicotinamide adenine dinucleotide (NAD) or nicotinamide adenine dinucleotide phosphate (NADP).

The fluorescent chromogen for use in the present invention is not limited as long as it fluoresces when reduced by the action of diaphorase in the presence of NADH (reduced NAD) or NADPH (reduced NADP). It is particularly desirable to use resazulin or alamar blue, because these substances have high fluorescence strength and are stable in air in both oxidized and reduced forms.

In addition, in order to improve the quantitative determination efficiency and recovery ratio of the substance to be measured (A), the diaphorase for use in the present invention may have a reaction equilibrium constant (K value) of 1 or more, preferably 10 or more, more preferably 100 or more, in the direction from the oxidized form of the fluorescent chromogen and the reduced form nicotine nucleotide (NADH or NADPH) toward the reduced form of the fluorescent chromogen and the oxidized form of the nicotine nucleotide (NAD or NADP).

It is desirable to blend these components in such amounts that the enzyme reaction from the cholesterol to the reduced form fluorescent chromogen progresses at a ratio of 90% or more, preferably 97% or more, more preferably 99% or more. For this purpose, diaphorase is used in an amount such that a diaphorase solution having a concentration of from 0.1 to 1,000,000 units per liter, preferably from 0.1 to 10,000 units per liter, more preferably from 1 to 1,000 units per liter, may be used in an amount of from 0.1 to 10,000 microliter, preferably from 1 to 1,000 microliter, more preferably from 1 to 100 microliter, per 100 $cm^2$ of the test strip. The dehydrogenase may be used in a concentration similar to that of the diaphorase. The NAD or NADP is used in an amount such that a solution having a concentration of from 0.001 nM (nanoMolar) to 200 mM (milliMolar), preferably from 0.1 nM (milliMolar) to 50 mM, may be used in an amount of from 0.1 to 10,000 microliter, preferably from 1 to 1,000 microliter, more preferably from 1 to 100 microliter, per 100 cm.² of the test strip.

The fluorescent chromogen may be used in an amount of from 0.01 to 500 mg, preferably from 0.1 to 100 mg, more preferably from 0.1 to 50 mg, per 100 cm² of the test strip. In this case, the amount of the fluorescent chromogen, if too small, would reduce fluorescence, and if too large, would result in an insoluble form and thus cause reduced accuracy.

This solution is deposited in a matrix within the dry strip to form an analysis pad for cholesterol, which fluoresces above a preset or predetermined concentration of cholesterol in the blood sample. The amount of reagent can be adjusted with respect to the concentration of the cholesterol to provide for fluorescence above about 180 milligrams/deciliter or 200 milligrams/deciliter, or above 240 milligrams/deciliter. Exact loadings may be routinely determined.

3. b. Triglyceride Determinations

Triglycerides are determined by first converting them to glycerols. When glycerol is being measured, oxidase and/or peroxidase enzymes are used. More particularly, when triglyceride is being measured, oxidase enzymes may be used in a reaction scheme where triglycerides are first converted to glycerol, and the glycerol concentration is determined as a marker for the triglycerides.

Accordingly, the present invention has been achieved by providing as a test strip element, an analysis pad that comprises a carrier, a dehydrogenase, diaphorase, a fluorescent chromogen and nicotinamine adenine dinucleotide (NAD) or nicotinamine adenonine dinucleotide phosphate (NADP).

The fluorescent chromogen for use in the present invention is one that fluoresces when reduced by the action of diaphorase in the presence of NADH or NADPH. It is particularly desirable to use resazulin or alamar blue, because these substances have high fluorescence strength and are stable in air in both oxidized and reduced forms.

In addition, in order to improve the quantitative determination efficiency and recovery ratio of the triglyceride, the diaphorase for use in the present invention may have a reaction equilibrium constant (K value) of 1 or more, preferably 10 or more, more preferably 100 or more, in the direction from the oxidized form of the fluorescent chromogen and the reduced form nicotine nucleotide (NADH or NADPH) toward the reduced form of the fluorescent chromogen and the oxidized form of the nicotine nucleotide (NAD or NADP).

It is desirable to blend these components in such amounts that the enzyme reaction from the triglyceride to the reduced form fluorescent chromogen progresses at a ratio of 90% or more, preferably 97% or more, more preferably 99% or more. For this purpose, diaphorase is used in an amount such that a diaphorase solution having a concentration of from 0.1 to 1,000,000 units per liter, preferably from 0.1 to 10,000 units per liter, more preferably from 1 to 1,000 units per liter, may be used in an amount of from 0.1 to 10,000 microliter, preferably from 1 to 1,000 microliter, more preferably from 1 to 100 microliter, per 100 cm² of the test strip. The dehydrogenase may be used in a concentration similar to that of the diaphorase. The NAD or NADP is used in an amount such that a solution having a concentration of from 0.001 nM (nanoMolar) to 200 mM (milliMolar), preferably from 0.1 nM (nanoMolar) to 50 mM (milliMolar), may be used in an amount of from 0.1 to 10,000 microliter, preferably from 1 to 1,000 microliter, more preferably from 1 to 100 microliter, per 100 cm² of the test strip.

The fluorescent chromogen may be used in an amount of from 0.01 to 500 mg, preferably from 0.1 to 100 mg, more preferably from 0.1 to 50 mg, per 100 cm² of the test strip. In this case, the amount of the fluorescent chromogen, if too small, would reduce fluorescence, and if too large, would result in an insoluble form and thus cause reduced accuracy. Preferably the amount of fluorescent chromogen should be such as to fluoresce at triglyceride concentrations above about 200 milligram/deciliter.

3. c. Low Density Lipoprotein (LDL Cholesterol) Determinations

Foltz et al. (U.S. Pat. No. 5,401,466) describes a dry phase sample strip for separating high density lipoprotein from a blood sample. This element may be used as an element 31 in the test strip 1. The strip has a first layer of fluid permeable material containing dispersed, finely divided, porous silica or silicate particles. These particles are adsorbent for the HDL. The particles are characterized by a size of from 1 to 1000 $\mu$ in their longest dimension and surface pores of from about 80 angstroms to 1000 angstroms. in size. The layer of silica or silicate containing material can be combined with a second layer 172 of a fluid permeable material bearing reagents for selectively removing very low density lipoproteins and chylomicrons from the blood sample and filtering the complex formed therein through a sub-micron filter to leave low density lipoprotein as the only lipoprotein in the blood sample. When these layers are combined with a third layer formed of a porous matrix containing a reagent system for the quantitative analysis of lipoprotein, the result is a unitary device for the one step determination of low density lipoprotein.

Determination of LDL cholesterol requires removal of erythrocytes and other lipid fractions from the blood sample before testing, only leaving only LDL cholesterol as the only macromolecule.

The use of particulate/porous silica gel immersed in a fluid permeable matrix to isolate LDL cholesterol results from a surface interaction with the silica as well as by size exclusion. The HDL component is removed by size exclusion and adsorption, i.e. the HDL is interactive with silica gel having a mean pore diameter greater than the diameter of an HDL particle, and is most useful when the silica pore size is small enough to diminish the interaction of the larger lipoprotein particles such as LDL and VLDL therewith. Silicas of particle size from about 1 to 1000$\mu$ (preferably 3 to 10 $\mu$) in their longest dimension and having a range of pore sizes of from 80 angstroms to 1000 angstroms (preferably 300 angstroms to 500 angstroms) are believed to have the best selectivity and efficiency for HDL particle removal.

The silica gel is entrapped in a porous layer, e.g., by formation of a fibrous network around the particles, as in the case of papers and felts, or by adhesively joining the silica to other fibers or particles which are incorporated easily into the matrix, e.g. by coating a fiber with an adhesive. Entrapment of the silica gel involving fibers may be assisted by a binder, such as starch or polyvinyl alcohol, to increase the durability of the silica containing layer. Glass is the preferred fiber. Other manmade fibers such as plastics containing hydrophilic groups or natural fibers such as cellulose, wool or silk can be used.

Ideally, the silica containing layer is combined with a separate fluid permeable layer of a matrix having dispersed therein reagents for the selective retention of VLDL and chylomicrons to ultimately provide, at the end of the stack or lamination of plies, layers, pads, or mats, a fluid sample containing only LDL. Suitable reagents for this part of the present system include a divalent cation and a polyvalent anion. The divalent cation is typically in the form of $MnCl_2$ or $MgCl_2$, and the polyvalent anion is typically heparin or dextran sulfate. A combination of heparin/$MnCl_2$ is preferred. While the serum or plasma sample being tested may be pretreated to remove VLDL and chylomicrons, a preferred technique involves dispersing the divalent cation/polyvalent anion combination in a porous matrix material such as glass fiber, cellulose or a felt or fabric of natural or man made fibers to provide a dry phase system for the VLDL/chylomicron removal step.

A dry reagent strip containing a stack, lamination, or train of layers, plies, or mats is used for determining LDL cholesterol in whole blood. Referring to FIG. 18, the stack, 63, consists of three layers for LDL selection; a glass felt containing porous silica for filtering red blood cells and capturing HDL, 63a, a glass fiber layer containing heparin and a manganese salt ($MnCl_2$), 63b, and a submicron filter layer, 63c. Beneath these layers, 63a, 63b, 63c, is a cholesterol indicating membrane, 63d, containing reagents for the breakup of lipoprotein particles, the conversion of cholesterol esters to cholesterol and an ultimate color reaction dependent upon cholesterol concentration.

This device allows blood to enter at the top of the stack which is positioned over a clear window so that color change can be measured in a small reflectance photometer. This color change is correlated to the lipoprotein remaining in the blood sample when it reaches the detection layer.

3. d. High Density Lipoproteins (HDL Cholesterol) Determinations

U.S. Pat. No. 5,135,716 to Thakore et al. describes an approach where the sample processing, including plasma separation, precipitant metering, precipitate separation as well as HDL cholesterol reactions are built into a dry body such that user manipulations are minimized and HDL cholesterol can be measured in one to two minutes directly from whole blood. The method measures the end-point of a chemical reaction and therefore precise time and temperature controls are not necessary. This method uses a simple device for separation of plasma and for measurement of cholesterol, and specific immobilized dry chemistry for HDL determination is used. The device employs a tangential flow of blood across the blood cell separation membrane. HDL dry chemistry precipitation reagents as well as precipitate filters are built into the device.

A test element, 64, according to Thakore et al. can be included in the dry test strip, 1. This element, 64, shown in FIG. 19, includes a multilayer structure with a microporous plasma separation membrane, 64a, at least one plasma collecting test membrane, 64b, a filtering membrane, 64c, and a layer, 64d, containing LDL and VLDL reactants to form LDL and VLDL precipitates and a carrier precipitation membrane, 64e.

The plasma collecting test membrane, 64b, has reactants which will react with HDL cholesterol and indicate the HDL cholesterol level quantitatively. The filtering membrane, 64e, may be located between the microporous plasma separation membrane and the transport medium or between the microporous plasma membrane and the plasma collecting test membrane and its function is to block the precipitated particles from reaching the test zone. The LDL and VLDL reactants which form precipitates of LDL and VLDL may be located anywhere upstream from the plasma collecting test membrane, i.e., within one or more of the transport medium, the microporous plasma separation membrane, the filtering membrane and the optional carrier separation membrane.

The microporous plasma separation membrane, 64a, has a nominal pore size of about 0.02 to about 10 microns.

Three precipitation systems may be used:
(1) Dextran sulfate (DS) (50,000 or 500,000 molecular weight) generally with magnesium chloride ($MgCl_2$) as the source for divalent cations;
(2) Heparin-manganese chloride; or
(3) Polyethylene glycol (6000 molecular weight).

The concentrations of the precipitant can be derived from those of liquid chemistries. However, in addition to the precipitants, it is advantageous to use hydrophilic non-volatile liquid or low molecular weigh additives such as low molecular weight polyethylene glycol (molecular weight 200–2000 or other similar polyhydroxyl compounds.) The polyethylene glycol is especially useful in a two-component precipitant system consisting of polymers and co-ions (e.g. DS-$MgCl_2$ and Heparin-$MnCl_2$). In such cases the salts and the polymers may adsorb differently to the membrane matrix. As a result, depending on the precipitant system and the membrane matrix, some trial and error approaches may be needed to determine the exact concentrations and the polymer:co-ion ratio if they are loaded in the absence of such hydrophilic components, since they may not be readily soluble in blood or plasma in a predictable manner. The non-volatile hydrophilic components (e.g. polyethylene glycol) keep the precipitants from adsorbing and from crystallizing and permit the movement of the precipitants in a predictable, readily soluble form for consistent release into the plasma (or blood). An additional advantage of polyethylene glycol is that it increases the "wettability" and serum uptake of a variety of membranes, particularly of cellulosic nylon and polysulfone types. polyethylene glycol (e.g. Of molecular weight of 400–2000) can be used in concentrations of 2–20% in water or buffer with 5–10% concentration being in the optimum range. The precipitants are dissolved in the aqueous polyethylene glycol solution at a concentration comparable to those used in liquid chemistry. For precipitation from whole blood, the precipitant concentration would be roughly half of that used in a plasma precipitation method. Typically, the membrane is saturated with the aqueous solution of polyethylene glycol with the dissolved precipitants and allowed to dry. Upon drying, the precipitant membrane is ready to use.

The plasma collecting test membrane or filtering/plasma receiving test membrane of the present invention device contains the enzymes cholesterol esterase, cholesterol oxidase and peroxidase along with buffer salts, activators, stabilizers and chromogen. The reagents are the same as those used in total cholesterol assays. The exact formulation is a matter of choice and also depends on the sources and purity of the enzymes. One typical formulation consists of cholesterol esterase (microbial @200 units/ml), cholesterol oxidase (Nocardia @40 units/ml), peroxidase (horseradish @200 units/ml) dissolved in 0.1M 2-[N-Morpholino]ethane sulfonic acid, potassium salt (MES) buffer at pH 6.7. The solution also contains 3% sodium cholate as activator. The reagent membrane is saturated with the enzyme solution, dried and then saturated in chromogen solution consisting of tetramethyl benzidine (TMB) and dioctysulfosuccinate, sodium salt (DOSS) at 5 mg/ml and 3 mg/ml respectively in acetone (or toluene) and allowed to dry.

The plasma reaching the analysis pad (now devoid of LDL and VLDL components) reacts with the reagents therein, producing a colored reaction, the intensity of color being proportional to HDL cholesterol concentration.

4. Hemoglobin ("Iron") Determinations

The mat or pad for analysis for hemoglobin and iron includes an acid buffer having a pH within the range of 2.5–5.0, a chromogen, a wetting agent, an agent capable of enhancing the peroxidase activity of hemoglobin, an organic hydroperoxide in the form of a stable, solid salt with an aliphatic, alicyclic or heterocyclic amine, and a solid, polymeric film-forming material or synthetic substance, the reagents being disposed upon an adsorbent bibulous carrier material.

The organic hydroperoxides suitable for use in hemoglobin analysis may conveniently be selected from among tertiary butyl hydroperoxide, phenylisopropylhydroxide, 4-methylphenylisopropyl hydroperoxide, phenyl-1,4-diisopropyl dihydroperoxide, 1-hydroxycyclohexyl-1-hydroperoxide, and 2,5-dimethylhexane-2,5-dihydroperoxide. As indicated above, the hydroperoxide is employed in the form of a stable, solid non-volatile salt with an aliphatic, alicyclic or heterocyclic amine. The amines found suitable for the purpose must evidence a pK of at least 8.0 and may be selected from among piperazine, (1,4, diazabicyclo-2,2,2-octane) octane, urea, hexamethylene tetramine, 2-amino-2-methyl-1,3-propandiol, 3,3'-diamino-2-propanol, 3,3'-diaminodipropylamine, mono and di-ethanolamine and cyclohexylamine. These salts are prepared by reacting the amine with the hydroperoxide.

The salts of organic hydroperoxides are used in a mixture with a 0.1 to 10 molar excess of the amine which stabilizes the hydroperoxide salt. While any of the above amines may be used in combination with any salt, a solid nonhygroscopic water soluble salt is preferred for use in a dry test strip.

The crystalline organic amine salts are carried in a non-aqueous solvent such as benzene, toluene, diethyl ether, chloroform, ethylenedichloride, petroleum ether, ethyl acetate and the like, with $C_1$–$C_3$ alkanols preferred The mat, pad, or layer for determination of hemoglobin also includes a polymeric, natural or synthetic filmforming organic substance which is capable of protecting the test area against the environmental deterioration. The organic substance employed must be water soluble, soluble in the described non-aqueous solvents, incapable of participating in the oxidation reaction and following evaporation of the solvent must be capable of forming a partially water wettable film on the bibulous carrier. Materials meeting these requirements are sodium alginate, polyvinylpyrrolidone, polyvinyl alcohol, starch, polyvinyl propionate, polyvinyl butyral, carboxymethyl cellulose, polyethylene glycols having a molecular weight within the range of 2,000–15,000 or mixtures of any of the foregoing.

Other components of the mat, pad, or layer constituting the test area may be selected from those materials known in the art for such purposes. For example, buffers comprising a mixture of a polyvalent organic or inorganic acid having a pK ranging from 1.0–5.0, sodium, potassium or ammonium salts thereof or mixtures of primary or secondary salts of such acids may be used. Typical of such buffers are mixtures of citric acid and sodium citrate, tartaric acid and sodium tartrate, malic acid and borax, potassium hydrogen phthalate and dipotassium phthalate, sodium hydrogen succinate and disodium succinate, and the like. The specific buffer chosen and the concentration thereof is not critical, the purpose of the buffer being the maintenance of a pH in the test pad, layer, or mat in the range of 2.5–5.0.

The wetting agent employed is designed to enhance the absorptivity of the test pad, mat, or layer and thereby increase the reaction rate. For this purpose any of the well-known anionic, nonionic or cationic detergents may be employed. A general preference has been found to exist for anionic detergents which are found to provide superior sensitivity.

Optionally, there may be included in the reagent combination an agent capable of enhancing the peroxidase activity of hemoglobin. Agents satisfying this requirement may be selected from among quinoline and its derivatives such as quinine, cinchonine, 6-methoxyquinoline, quinaldine, 8-amino-6-methoxy-quinoline, 2-quinolinol and the like. The presence of such reagents accelerates the rate of the oxidation reaction and enhances the color intensity of the oxidized chromogen which yields higher sensitivity.

5. Thrombin ("Clotting Factor") Determinations

Clotting factor is determined using a mat or pad containing partial thromboplastin, contact activators, a chromophoric thrombin substrate, phospholipid and $Ca^{2+}$, the contact activator preferably being ellagic acid.

The dry reagent is a single mat, pad, carrier material, or reaction: matrix, which contains a blood coagulation factor or co-factor and a buffer substance. Additionally, the dry reagent may also contain a second carrier material with an oxidation agent. In this case, the first carrier material contains an aniline or phenol derivative forming a color with the chromophore of the chromophoric substrate in the presence of the oxidation agent of the second carrier material.

The dry reagent can contain any desired chromophoric substrate of a protease of the blood coagulation system. As chromophoric substrates in the scope of the present invention, there have proved to be well suited compounds of the general formula

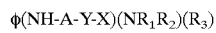

$\phi(NH-A-Y-X)(NR_1R_2)(R_3)$ where $\phi$ is the aryl group, and in which A is the amino acid arginine or lysine, X is an N-terminal amino acid protective group, Y is a single bond or a chain of 1 to 3 amino acids, $NR_1R_2$ is a group in the o or p-position in which $R_1$ and $R_2$, independently of one another, are hydrogen atoms or alkyl radicals containing up to 3 carbon atoms or a nitro group and $R_3$ is a hydrogen atom, a carboxylic ester or carboxylamido group, a halogen atom, a nitro group or an alkyl radical containing up to 3 carbon atoms.

A chromophoric substrate in which X-Y-A represents Tos-Gly-Pro-Arg is especially preferred.

As color-forming aniline or phenol derivative, such compounds as N-methylanthranilic acid, dimethylanthranilic acid, N-ethyl-N-(3'-sulphobenzene)-aniline and 2,3-xylenol can be used.

In the case of the preferred embodiment of the present invention, which contains a second absorbent carrier material impregnated with an oxidation agent, the first absorbent carrier material is preferably impregnated with Tos-Gly-Pro-Arg-p-phenylenediamine as chromophoric substrate and N-methylanthranilic acid as color-forming aniline derivative and the second absorbent material contains potassium ferricyanide as oxidation agent.

The reagent bearing analysis pad, mat, or layer used in the present invention can be used for determination with plasma or with whole blood. If the determination is carried out with whole blood, it is preferable additionally to provide a third absorbent mat or pad interposed to intercept the flow of blood solids.

The absorbent mat or pad is preferably an absorbent, swellable or soluble film-forming carrier material, such as paper and similar fleece materials, for example tea bag paper, filter paper, and the like.

6. Supporting The Multi-Layers: The support member or members which hold the individual multi-layers (test elements), 61, 71, of the test strip, 1, as well as the individual (glucose, glycosylated hemoglobin, LDL cholesterol, HDL cholesterol, triglycerides, etc.) laminates in the test strip can be opaque, reflective, or transparent to light or other energy. The support member(s) will be compatible with the intended analysis mode and indicator used (such as chromogenic or fluorescence indicators). Materials that can be used for the support members include a variety of plastics and polymers such as cellulose acetate, polyester, polycarbonate, polyvinylchloride, polyethylene, and polystyrene. Generally, where such materials are used, the support member is substantially planar.

The multi-layer test strip 21 has at least one support member with a detection aperture below the indicator layer. This means that where the one support member is transparent, there is no need for a detection aperture whereas with a non-transparent support member a detection aperture is needed and present. The detection aperture is a hole for observing the color transition or fluorescence on the indicator layer. The size of the aperture is generally smaller than the size of the multi-layers and its size depends on the size of the layer or layer pads. The aperture size will generally be from 0.5 to 10 mm, preferably between 1 and 5 mm. The position of the detection aperture on the bottom support member depends upon whether the multi-layers are superposed or juxtaposed. Where the multi-layers are superposed, the detection aperture is below all of the multi-layers. Where the multi-layers are juxtaposed, the detection aperture is directly below only the indicator layer or other final layer.

7. Reflectance Meter

The reflectance meter, 201, useful in association with the test strip, 1, illuminates the individual analysis elements, 61, 71, through the apertures 31, 33 of the test strip, 1, to determine an optical property of the reacted blood component, and thereby the concentration thereof. In detector circuits, 201, useful in the practice of the invention, the output of the detector, 217a, 217b, is passed to an amplifier, 219a, 219b, for example, a linear integrated circuit which, converts the phototransistor current to a voltage. The output of the amplifier, 219a, 219b, can be fed to a processor or a track and hold circuit, 221a, 221b. The combination of the amplifier, 219a, 219b, and the track and hold circuit, 221a, 221b, is a combination linear/digital integrated circuit which tracks or follows the analog voltage from the amplifier and, upon command from the microprocessor, locks or holds the voltage at its level at that time.

An analog-to-digital converter, 223a, 223b, takes the analog voltage from the track and hold circuit, 221a, 221b, and converts it to a binary digital number upon command of the microprocessor, 501. The microprocessor, 501, can be a digital integrated circuit. The microprocessor provides at least the following control functions: 1) timing for the entire system; 2) reading of the output of analog/digital converter; 3) program, 4) data memory for storing data corresponding to the reflectance measured at specified time intervals; 5) calculating component levels from the stored reflectances; and 6) outputting blood component concentration data to a display and/or to a RAM (with identifying data), 301.

The memory can be a digital integrated circuit which stores data, 301, and the microprocessor operating program, 251. Reporting can be to a memory circuit, to a display circuit, or to a communications circuit, or to any or all of them. Usually reporting is a visual display, such as a liquid crystal display (LCD) or a light emitting diode (LED) display. It can also be a RAM for storing a database of other blood fraction concentrations and identifying data. The instrument also can include a start-stop switch and can provide an audible or visible time output to indicate times for applying samples, taking readings etc., if desired.

The reflectance circuit itself can be used to initiate timing by measuring a drop in reflectance that occurs when the aqueous portion of the blood applied to the porous matrix, or reagent pad migrates through the matrix to the surface or zone at which reflectance is being measured. Typically, the measuring device is turned on in a "ready" mode in which reflectance readings are automatically made at closely spaced intervals (typically about 0.2 seconds) from the typically off-white, substantially dry, unreacted reagent strip. The initial measurement is typically made prior to penetration of the matrix by the blood being analyzed. The reflectance value is evaluated by the microprocessor, typically by storing successive values in memory and then comparing each value with the initial unreacted value. When the blood penetrates the reagent matrix pad, the drop in reflectance signals the start the measuring time interval. Drops in reflectance of 5–50% can be used to initiate timing, typically a drop of about 10% initiates timing. In this simple way there is exact synchronization of blood reaching the surface from which measurements are taken and initiation of the sequence of readings, with no requirement of activity by the user.

The meter, 201, a diffuse reflectance spectrophotometer with appropriate software, automatically reads a time series of reflectance data for the exposed test pads, calculates rates of reflectance change, and, using calibration factors, outputs the level of specific blood components. One example of such a device is shown in FIG. 9 and FIG. 10 where a test strip, 1, is in the meter, 201. A light source, 205, for example a high intensity light emitting diode (LED), a laser, an incandescent lamp, or a vapor lamp, projects a beam of light onto the reagent pads, 41, 61, of the test strip. A portion of this light is diffusively reflected from the analysis pads, 41, 61, of the test strip, 1, and is detected by light detectors, for example a phototransistor that produces an output current proportional to the light it receives. Both the light source and/or the detector can be adapted to generate or respond to a particular wavelength light, if desired.

The microprocessor, 501, serves the following control functions: (1) multiplexing the light sources and light detectors and the track and hold circuits for the plurality of light sources and associated test pads on the test strip, (2) timing for the entire system; (3) reading of the output of analog/digital converters; (4) storing data corresponding to the reflectance measured at specified time intervals; (5) calculating analyte levels from the stored reflectances; and (6) outputting blood component concentration data to the display and/or other output devices. Memory can be a digital integrated circuit which stores data and the microprocessor operating program. In a preferred embodiment of the invention, the readings are stored in a database or spread sheet or other data structure for transfer to a host computer. Reporting device can take various hard copy, soft copy, and electronic forms 8. Reflectance Switching The reflectance circuit can be used to initiate timing by measuring a drop in reflectance that occurs when the blood reaches the analysis or test pad or mat, and thereafter migrates to the surface at which reflectance is being measured. Typically, the measuring device is turned on in a "ready" mode in which reflectance readings are automatically made at closely spaced intervals from the substantially dry, unreacted reagent analysis or test strip, pad, or mat. The initial measurement is made before blood reaches the mat, pad, or matrix. The reflectance value is evaluated by the microprocessor, for example, by storing successive values in memory and then comparing each value with the initial unreacted value. When the blood penetrates the analysis or test mat or pad, 1, and the reacted blood component is visible through the apertures 31, 33, the initial drop in reflectance signals the start of the measuring time interval.

9. Data Collection and Reporting

Data is initially collected in the meter, 201, itself. The data may be in the form of a spread sheet or database. The database may be a linked list or a relational database. In the case of a relational database, the metadata of the database would include time of sample analysis, and the concentrations of each fraction measured, as well as times of measuring other components and inputs, and the values thereof, or the values of coefficients of compressed inputs, such as electrocardiogram traces. Data could then be extracted and reported in tabular format, or graphically.

A further aspect of the data collection and reporting is that the data can be uploaded to a host computer, as a personal computer, or directly to a health care provider, e.g., as a server or a web server.

FIG. 10 through FIG. 16 illustrate the data management, data interfaces, and data transmission aspects of the invention.

FIG. 10 illustrates the integrated system where a test strip or sample pad 1 receives a "pin prick" or "stick pin" sample of blood through the sample receiving aperture 21 to sample receiving pad 41. The blood sample moves, e.g., by capillary action, hydrophobicity, and surface tension, through the sample distributor, divider, or distribution network 51 to sample analysis pads, e.g., pads 61 and 81, which are exposed through openings 31 and 33. The sample analysis pads, 61 and 81, are fluidically in series with the sample receiving pad 41, and fluidically in parallel with each other, as clearly shown in FIG. 1 and in FIG. 4, FIG. 5, and FIG. 10.

The test strip 1 is logically and optically in series with the meter 201, through optics 211a and 211b, The optical system includes light sources 215a and 215b, and detectors 217a and 217b, under the timing control of a microprocessor 501. The light signals received by the detectors 217a and 217b and amplified in amplifiers 219a and 291b, held in tarch and hold elements 221a and 221b, and digitized in analog/digital converters 223a and 223b.

The digitized signals travel through the data and control bus. The data and control bus also carries user input 271 (on, off, blood component or date to be displayed, etc.), a program memory 251 (which may be RAM or ROM, or ROM opened into RAM), data memory 301 (which may be volatile RAM or powered persistent RAM), a display 261, and I/O 401 (e.g., to a host computer or to telecommunications systems).

FIG. 11 illustrates a memory management system, including schema and metadata, using, solely by way of illustration and not limitation, the memory structure of Microsoft Windows CE. The memory 301 has records 311a, 311b, and 311c. Each of the records, 311a, 311b, 311c, has "Properties" 321a, 322a, 323a, and 321b, 322b, 323b, and 321c, 322c, and 323c. In accordance with the Microsoft Windows CE programming paradigm, the "Properties" include "ID" (as glucose, glycosolated hemoglobin, triglycerides, cholesterol, LDL cholesterol, HDL cholesterol, clotting factor, and hemoglobin/iron), the "Type" (integer, long integer, floating point, long floating point, constant), and "Value", the actual data value.

Alternatively, the memory management system may use a spread sheet paradigm, with rows being "files" and columns being "data", as illustrated in FIG. 12. As there shown, there are two records, 311a and 311b, with a data column (integer data), 321a and 321b, a "glucose" data column (floating point), 322a and 322b, a cholesterol data column (floating point), 323a abd 323b, and a glycosolated hemoglobin data column (floating point) 324a and 324b.

It is, of course, to be understood that various database and/or spreadsheet paradigms, with various schema and metadata may be utilized without departing from the central inventive concepts.

FIG. 13, FIG. 14, and FIG. 15 illustrate synchronization with hosts or servers and data transmission to hosts and servers, as well as with peripherals, such as blood pressure, pulse, respiration, and electrocadiogram inputs. FIG. 13 illustrates a data synchronization method similar to that used between a Microsoft Windows CE palmtop or handheld device and a personal computer using the Microsoft Mobile Devices application. As shown in FIG. 13, a communications link is established between the pc host and the meter 421. The PC then accesses the database on the meter 423. The first task is determining if a file object on the meter has been created or changed since the last synchronization 425. If so, the created and/or changed data objects are enumerated, 427, and the meter notified of the enumerated file object or objects 429. The meter selects a file object for synchronization 431. The selected file object is serialized 433 and sent from the meter to the personal computer 435. The personal computer deserializes the file object and stores it in a database on the personal computer 437. After the last file object is synchronized, the connection is closed 439.

FIG. 14 and FIG. 15 illustrate two alternatives for transferring data between the meter 201 and a health care provider. In FIG. 14 the data is transferred via a PC, while in FIG. 15 the data is transferred directly from the meter 201.

FIG. 14 illustrates a meter 201 with an operating system synchronization interface 411 interposed between the meter 201 and a Personal Computer 400. The data is synchronized to the Personal Computer 400, and then through an FTP or HTTP layer 451, and a TCP/IP layer 453, to a web server 455. The web server 455 passes the data to an application server 457 and an associated database server 459. The application server 457 passes the data to a web server 461, a TCP/IP layer 463, and an HTTP or FTP layer 465 to a host computer 467 for the health care provider.

FIG. 15 illustrates an alternative system where the meter has web browser capability, at least insofar as transmitting data to a web server. The FIGURE illustrates a meter 201 with an FTP or HTTP layer 451', and a TCP/IP layer 453', passing data to a web server 455'. The web server 455' passes the data to an application server 457' and an associated database server 459'. The application server 457' passes the data to a web server 461', a TCP/IP layer 463', and an HTTP or FTP layer 465' to a host computer 467' for the health care provider.

10. Scalability of Data Collection and Reporting

FIG. 16 illustrates the scalability of the method of the invention. For example, the database 399 could have schema and metadata to be easily scalable, taking digitized 301 blood chemistry data from the meter 201 described above, digitized 503 blood pressure, pulse, and/or respiration data 501, and digitized and (optionally) compressed 603 electrocardiogram data 601. The database 399 is scaled to include blood pressure and electrocardiogram data. This data could be collected at the meter 201 through a serial or parallel port (indicated as I/O element 401 in FIG. 10). This data may then be sent via a network, as shown in FIG. 14 and FIG. 15, to a health care provider 467 or 467'. The blood pressure and electrocardiogram data may be collected during, for example, exercise (as on a rowing machine, a stair climber machine, a tread mill, or aerobic exercise, or the like) and loaded into the meter 201 or 401.

The electrocardiogram data may be taken from less then five leads, and is preferably compressed (shown as "Fourier (cardiogram)" in FIG. 16). Compression of electrocardiogram data is well know, and is illustrated, for example in U.S. Pat. No. 4,947,858, the disclosure of which is incorporated herein by reference.

U.S. Pat. No. 4,947,858 to Smith for "Method And Apparatus For Data Compression In An ECG Monitoring System" describes a data compression method that includes the steps of conditioning the analog input ECG beats into filtered digital data; identifying the individual QRS peaks in the beats; and compressing the beats. Specifically, the step of compressing a beat includes selectively sub-sampling the beat; template matching and differencing the beat with a template beat, namely the immediately preceding beat of its type (normal, ectopic or artifact); and coding the sub-sampled differenced beat.

Smith describes the step of selective sub-sampling as including dividing the QRS region into at least two sub-regions centered about the QRS peak; and selectively sub-sampling each sub-region at a different compression ratio.

While the invention has been described with respect to certain preferred embodiments and exemplifications, it is not intended to limit the scope of the invention thereby, but solely by the claims appended hereto.

I claim:

1. A method of measuring, digitizing, and storing blood component data comprising the steps of:

(a) depositing a blood sample on a test strip having two or more distinct regions for detecting and indicating the presence and concentration of blood fractions including (i) blood glucose and (ii) at least one other blood component chosen from the group consisting of glycosylated hemoglobin, cholesterol, LDL cholesterol, HDL cholesterol, triglycerides, hemoglobin, and clotting factors; said test strip having at least one portion for measuring blood glucose, said portion comprising a fibrous, polyamide matrix containing immobilized glucose oxidase and immobilized glucose peroxidase;

(b) measuring, digitizing, and storing indications of blood fraction concentration in an associated meter configured to read blood fraction presence and concentration indications, digitize the indications, store the digitized indications, and transmit the digitized indications; and (c) transmitting the stored indications of blood fraction indication to a server.

2. A method of analyzing, measuring, recording, and uploading biological functions comprising the steps of:

(a) analyzing a blood sample from a subject for concentrations of components thereof including (i) blood glucose and (ii) at least one other blood component chosen from the group consisting of glycosylated hemoglobin, cholesterol, LDL cholesterol, HDL cholesterol, triglycerides, hemoglobin, and clotting factors; said test strip having at least one portion for measuring blood glucose, said portion comprising a fibrous, polyamide matrix containing immobilized glucose oxidase and immobilized glucose peroxidase;

(b). recording the concentrations in a memory;

(c) measuring and recording cardiovascular measures of the subject chosen from the group consisting of blood pressure, respiration rate, and electrocardiogram in the memory; and (d) uploading the recorded blood component concentrations and cardiovascular measures to a remote server.

3. The method of claim 2 comprising determining the blood component concentrations by the method of:

(a) depositing a blood sample on a test strip having two or more distinct regions for detecting and indicating the presence and concentration of blood fractions; and (b) measuring, digitizing, and storing indications of blood fraction concentration in an associated meter configured to read blood fraction presence and concentration indications, digitize the indications, store the digitized indications, and transmit the digitized indications.

4. The method of claim 2 wherein the cardiovascular measure is an electrocardiogram, and the electrocardiogram is compressed before transmission to the server.

* * * * *